United States Patent
Abraham et al.

(10) Patent No.: US 10,751,361 B2
(45) Date of Patent: Aug. 25, 2020

(54) ENHANCED IMMUNE RESPONSE IN BOVINE SPECIES

(71) Applicant: Bayer Animal Health GmbH, Leverkusen (DE)

(72) Inventors: Albert Abraham, Shawnee, KS (US); Daniel Keil, SpringHill, KS (US); Jason Nickell, Parkville, MO (US); Christian Weiss, Leverkusen (DE)

(73) Assignee: BAYER INTELLECTUAL PROPERTY GMBH, Monheim (DE)

( * ) Notice: Subject to any disclaimer, the term of this patent is extended or adjusted under 35 U.S.C. 154(b) by 0 days.

(21) Appl. No.: 16/058,888

(22) Filed: Aug. 8, 2018

(65) Prior Publication Data

US 2019/0201434 A1    Jul. 4, 2019

Related U.S. Application Data

(63) Continuation of application No. 13/923,496, filed on Jun. 21, 2013, now abandoned, which is a continuation of application No. PCT/EP2011/073414, filed on Dec. 12, 2011.

(60) Provisional application No. 61/426,255, filed on Dec. 22, 2010.

(51) Int. Cl.
| | | |
|---|---|---|
| A61K 39/00 | (2006.01) |
| A61K 39/38 | (2006.01) |
| A61K 31/711 | (2006.01) |
| A61K 9/127 | (2006.01) |
| A61K 39/102 | (2006.01) |
| A61K 9/00 | (2006.01) |
| A61K 39/39 | (2006.01) |
| A61K 45/06 | (2006.01) |

(52) U.S. Cl.
CPC .......... *A61K 31/711* (2013.01); *A61K 9/0019* (2013.01); *A61K 9/1272* (2013.01); *A61K 39/102* (2013.01); *A61K 39/39* (2013.01); *A61K 45/06* (2013.01); *A61K 9/1271* (2013.01); *A61K 2039/552* (2013.01); *A61K 2039/55555* (2013.01); *A61K 2039/55566* (2013.01)

(58) Field of Classification Search
CPC . A61K 9/1271; A61K 2039/552; A61K 38/00
See application file for complete search history.

(56) References Cited

U.S. PATENT DOCUMENTS

| | | |
|---|---|---|
| 3,854,480 A | 12/1974 | Zaffaroni |
| 4,452,775 A | 6/1984 | Kent |
| 4,675,189 A | 6/1987 | Kent et al. |
| 5,075,109 A | 12/1991 | Tice et al. |
| 5,133,974 A | 7/1992 | Paradissis et al. |
| 5,407,686 A | 4/1995 | Patel et al. |
| 5,427,791 A | 6/1995 | Ahmad et al. |
| 5,736,152 A | 4/1998 | Dunn |
| 5,830,878 A | 11/1998 | Gorman et al. |
| 6,048,535 A | 4/2000 | Sharma |
| 6,207,646 B1 | 3/2001 | Krieg et al. |
| 6,239,116 B1 | 5/2001 | Krieg et al. |
| 6,406,702 B1 | 6/2002 | Sharma |
| 6,429,199 B1 | 8/2002 | Krieg et al. |
| 6,693,086 B1 | 2/2004 | Dow et al. |
| 7,056,492 B2 | 6/2006 | Gorman et al. |
| 2003/0022854 A1 | 1/2003 | Dow et al. |
| 2003/0191082 A1 | 10/2003 | Wheeler |
| 2004/0002472 A1 | 1/2004 | Audonnet et al. |
| 2004/0247662 A1 | 12/2004 | Dow |
| 2005/0191342 A1 | 9/2005 | Tam et al. |
| 2006/0223769 A1 | 10/2006 | Dow et al. |
| 2007/0134200 A1 | 6/2007 | Eldridge et al. |
| 2009/0263423 A1* | 10/2009 | Fairman ............ A61K 39/0208 424/209.1 |
| 2011/0111017 A1 | 5/2011 | Bosio |
| 2012/0064151 A1 | 3/2012 | Abraham |
| 2013/0295167 A1 | 11/2013 | Abraham et al. |

FOREIGN PATENT DOCUMENTS

| | | |
|---|---|---|
| CL | 00065 | 1/2011 |
| WO | WO 9966879 | 12/1999 |
| WO | 2002086101 A2 | 10/2002 |
| WO | WO 2005079506 | 9/2005 |
| WO | WO 2007117303 | 10/2007 |
| WO | WO 20090120811 | 10/2009 |
| WO | WO 20101303374 | 11/2010 |
| WO | WO 2012084951 | 6/2012 |

OTHER PUBLICATIONS

Rice et al., Animal Health Research Reviews, 2007; 8(2): 117-128 (Year: 2007).*

Angen, O, et al., "Taxonomic relationships of the [Pasteurella] haemolytica complex as evaluated by DNA-DNA hybridizations and 16S rRNA sequencing with proposal of Mannheimia haemolytica gen. nov., comb. nov., Mannheimia granulomatis comb. nov., *Mannheimia glucosida* sp. nov., *Mannheimia ruminalis* sp. nov. and *Mannheimia varigena* sp. nov.," 1999. Int'l J. Systematic Bacteriology, 49:67-86.

Babiuk, L.A., "Broadening the Approaches to Developing More Effective Vaccines," 1999, Vaccine, 1587-1595, 9 pages.

Buttaro, C., et al , "Engineered *E coli* as Vehicles for Targeted Therapeutics," 2010, Current Gene Therapy, 10:27-33.

Cornelie, J. et al, Methylated CPG-Containing Plasmid Activates the Immune System; Scandinavian Journal of Immunology, 2004, vol. 59, No. 2, pp. 143-151.

(Continued)

*Primary Examiner* — Gary B Nickol
*Assistant Examiner* — Lakia J Jackson-Tongue
(74) *Attorney, Agent, or Firm* — McBee Moore & Vanik IP, LLC

(57) ABSTRACT

The present invention relates to a method of immune activation which is effective for eliciting a non-antigen-specific immune response in a member of the bovine species. The method is particularly effective for protecting a member of the bovine species from infectious disease and treating animals inflicted with infectious disease.

10 Claims, 27 Drawing Sheets

(56) References Cited

OTHER PUBLICATIONS

Dow, et al, "Liposome-Nucleic Acid Immunotherapeutics," 2008, Expert Opinion Drug Delivery, 5/1: 11-24.
Dow, et al., "Lipid-DNA Complexes Induce Potent Activation of Innate Immune Responses and Antitumor Activity When Administered Intravenously," 1999, J Immunology 163:1552-1561.
Gomis, S. et al, Protection of Chickens Against *Escherichia coli* Infections by DNA Containing CPG Motifs; Infection and Immunity, (Feb. 2003), vol. 71, No. 2, pp. 857-863.
Gomis, S. et al, Protection of Neonatal Chicks Against a Lethal Challenge of *Escherichia coli* Using DNA Containing Cytosine-Phosphodiester-Guanine Motifs; Avian Diseases, (2004), 48, pp. 813-822.
Gomis, S. et al., Protection of chickens against a lethal challenge of *Escherichia coli* by a vaccine containing CPT Oligodeoxynucleotides as an adjuvant. Avian Diseases, 2007, 78-83.
Gursel, I., et al., Sterically Stabilized Cationic Liposomes Improve the Uptake and Immunostimulatory Activity of CPG Oligonucleotides; Journal of Immunology, 2001, vol. 167, No. 6, pp. 3324-3328.
International Search Report dated Aug. 6, 2010, issued in PCT/EP2010/002809, 8 pgs.
Levesque, S., et al, Improvement of Adjuvant Systems to Obtain a Cost-Effective Production of High Levels of Specific IGY; Poultry Science, 2007, vol. 86, No. 5, pp. 630-635.
Morrey et al.,. "Efficacy of Cationic Lipid-DNA Complexes (CLDC) on Hepatitis B Virus in Transgenic Mice," 2008, Antiviral Res., 79:71-79.
Nichani, A.K., Subcutaneous, but not Intratracheal Administration of the TLH9 Agonist, CPG DNA Transiently Reduces Parainfluenza-3 Virus Shedding in Newborn Lambs; Comparative Immunology, Microbiology and Infectious Diseases, (2010), 33, pp. E111-E117.
Olsson, B., et al., "Chapter 2 Pulmonary Drug Metabolism, Clearance, and Absorption," 2011, Controlled Pulmonary Drug Delivery, Advances in Delivery Science and Technology, H.D.C. Smyth, and A.J. Hickey, Eds., XIV, pp. 21-50.
Patel, B.A., et al., Oligodeoxynucieotides Containing CPG Motifs (CPG-ODN) Predominantly Indue TH1-Type Immune Response in Neonatal Chicks; Developmental and Comparative Immunology, (2008), 32, pp. 1041-1049.
Penha Filho, R.A., et al., Control of *Salmonella enteritidis* and *Salmonella gallinarurn* in Birds by Using Live Vaccine Candidate Containing Attenuated *Salmonella gallinarum* Mutant Strain; Vaccine, (2010), 28. pp. 2853-2859.
Rice, J. A. et al, "Mannheimia haemolytica and bovine respiratory disease", Animal Health Research Reviews 8(2); 2008, 117-128.
Sambrook, J., et al., Molecular Cloning a Laboratory Manual, Cold Spring Harbor Laboratory Press, (1989), 2nd Ed., pp. 4.22-4.23 & pp. 4.37-4.38.
Suarez, D.L., et al., "The Effect of Eukaryotic Expression Vectors and Adjuvants on DNA Vaccines in Chickens Using an Avian influenza Model," 2000, Avian Diseases, 44/4:861-868.
Taghavi, A., et al., Enhancement of Immunoprotective Effect of CPG-ODN by Formulation with Polyphosphazenes Against *E. coli* Septicemia in Neonatal Chickens; Current Drug Delivery, (2009). 6, pp. 76-82.
Taghavi, Azita, "Immunostimulatory effects and delivery of oligodeoxynucleotides containing CpG motifs (CpG-ODN) in neonatal broiler chickens", Thesis, University of Saskatchewan, Apr. 2008, 175 pages.
The Merck Veterinary Manual: http://www.merckmanuals.com/vel/respiratory_system/respiratory_diseases_of_cattle/bacterial_pneumonia_in_cattle.html, accessed Nov. 21, 2014.
Verminnen, K. et al., Vaccination of Turkeys Against Chlamydophila Psittaci Through Optimised DNA Formulation and Administration; Vaccine, 2010, vol. 28, No. 18, pp. 3095-3105.
Wamer et al., "Recombinant DNA Advisory Committee, Protocol Review #0808-934 and #0808-936," Dec. 3, 2008, 93 pages.
Zaks, et al, "Efficient Immunization and Cross-Priming by Vaccine Adjuvants Containing TLR3 or TLR9 Agonists Complexed to Cationic Liposomes," 2006, J Imrnunol, 176:7335-7345, 12 pages.
Zoetis; Pneumonia—Bovine Respiratory Disease—Dairy (BRD), www.zoetis.comau/diseases/215/pneumonia, downloaded Jan. 24, 2014, 4 pages.

* cited by examiner

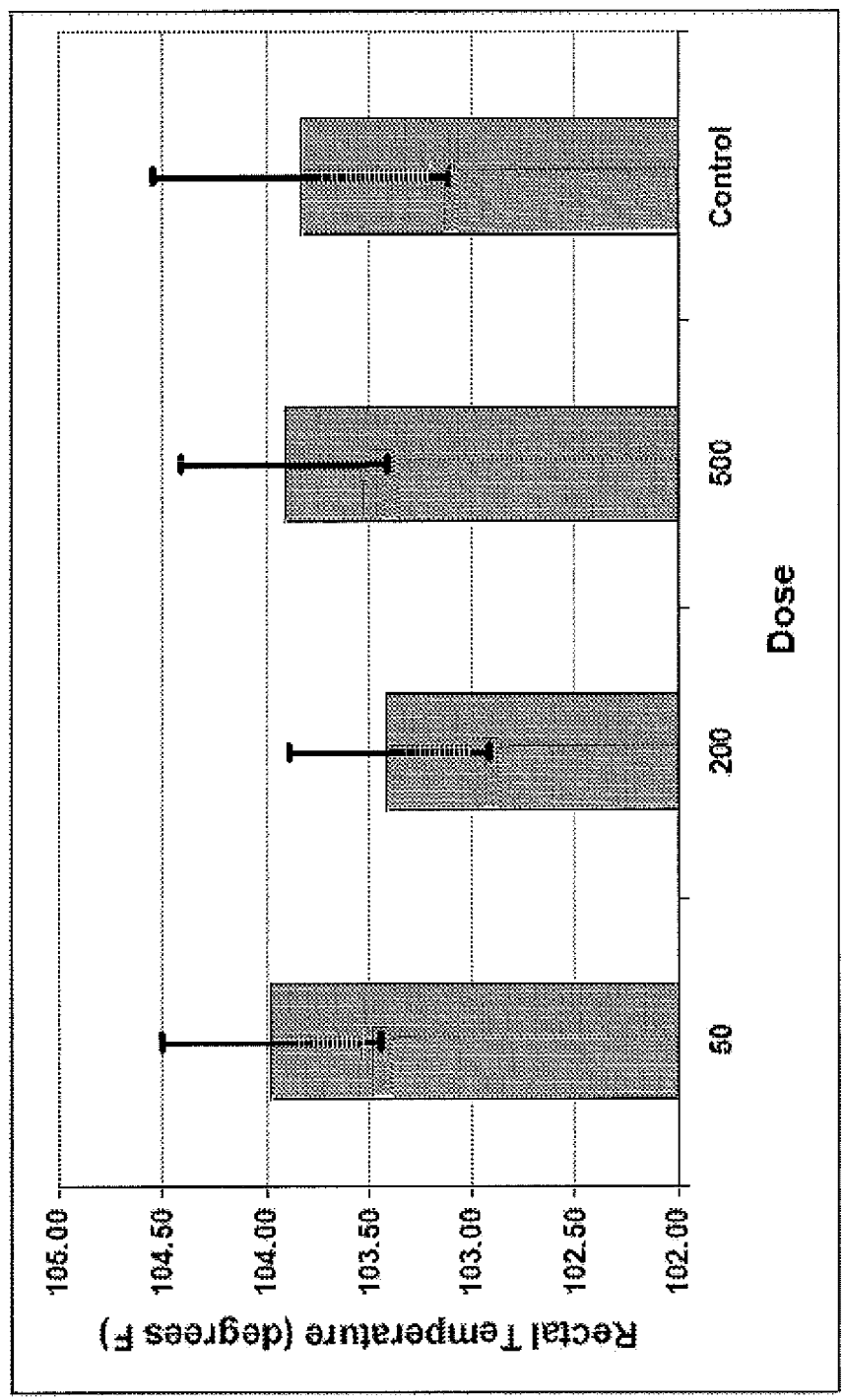
FIG. 1.1

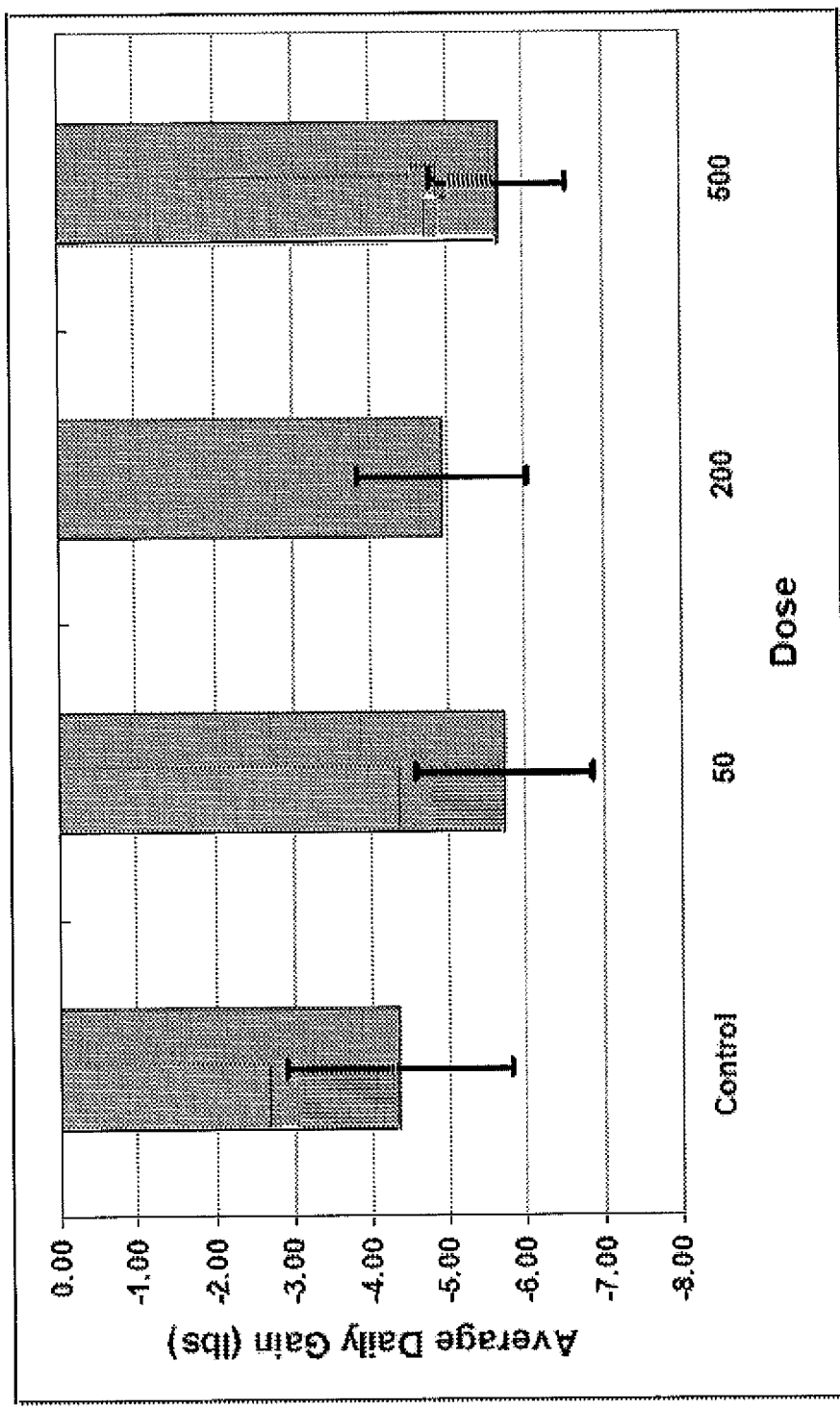
FIG. 1.2

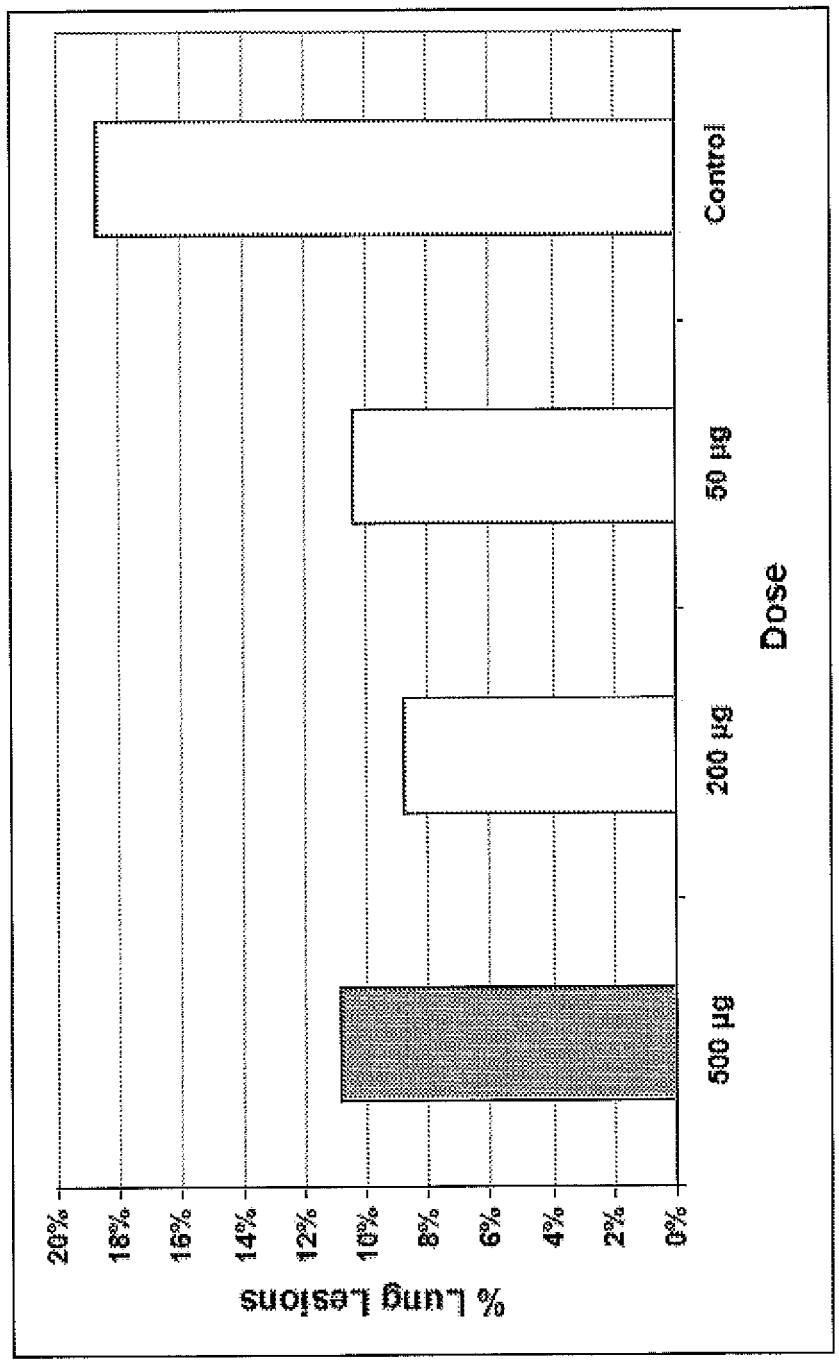
FIG. 1.3

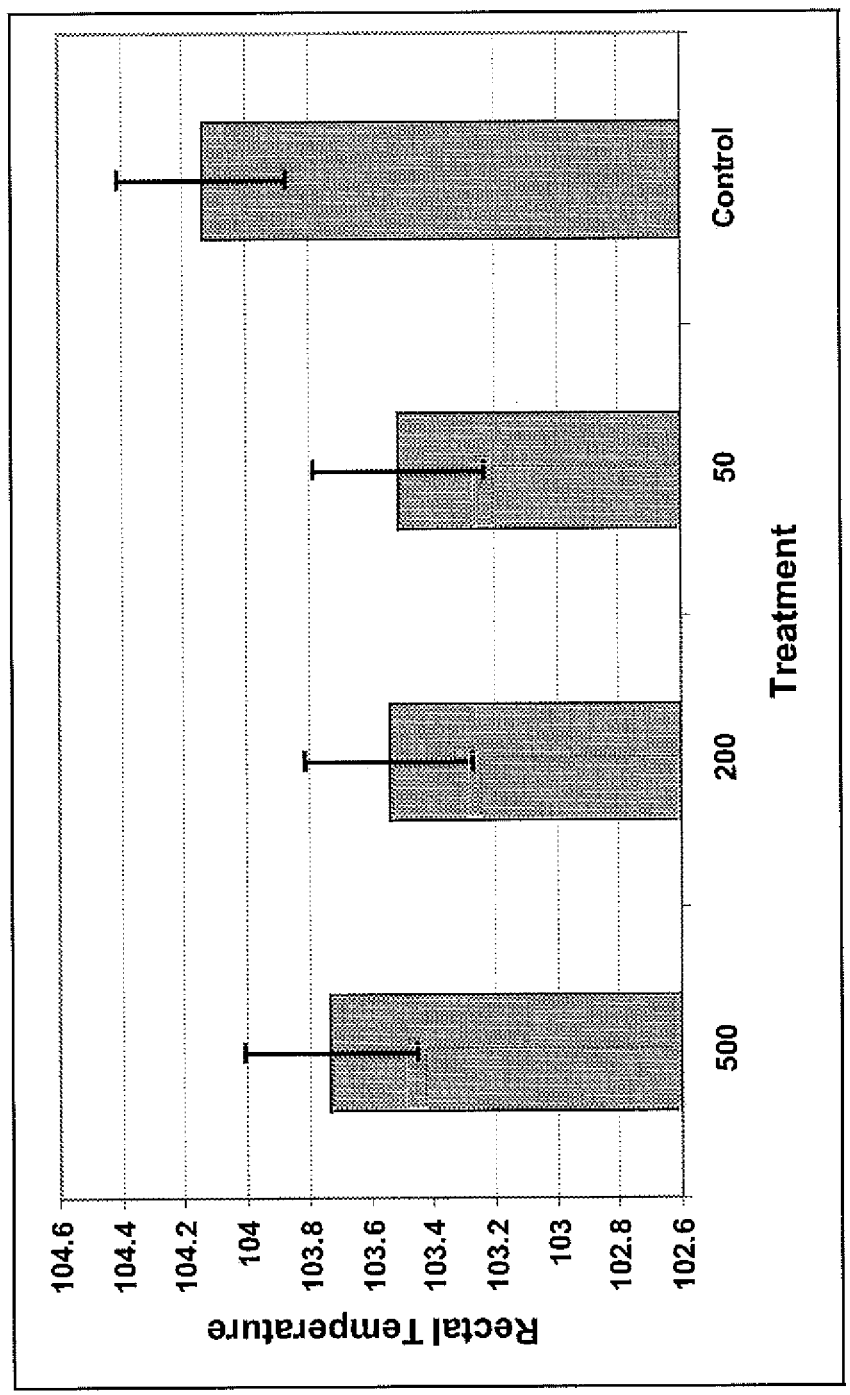
FIG. 2.1

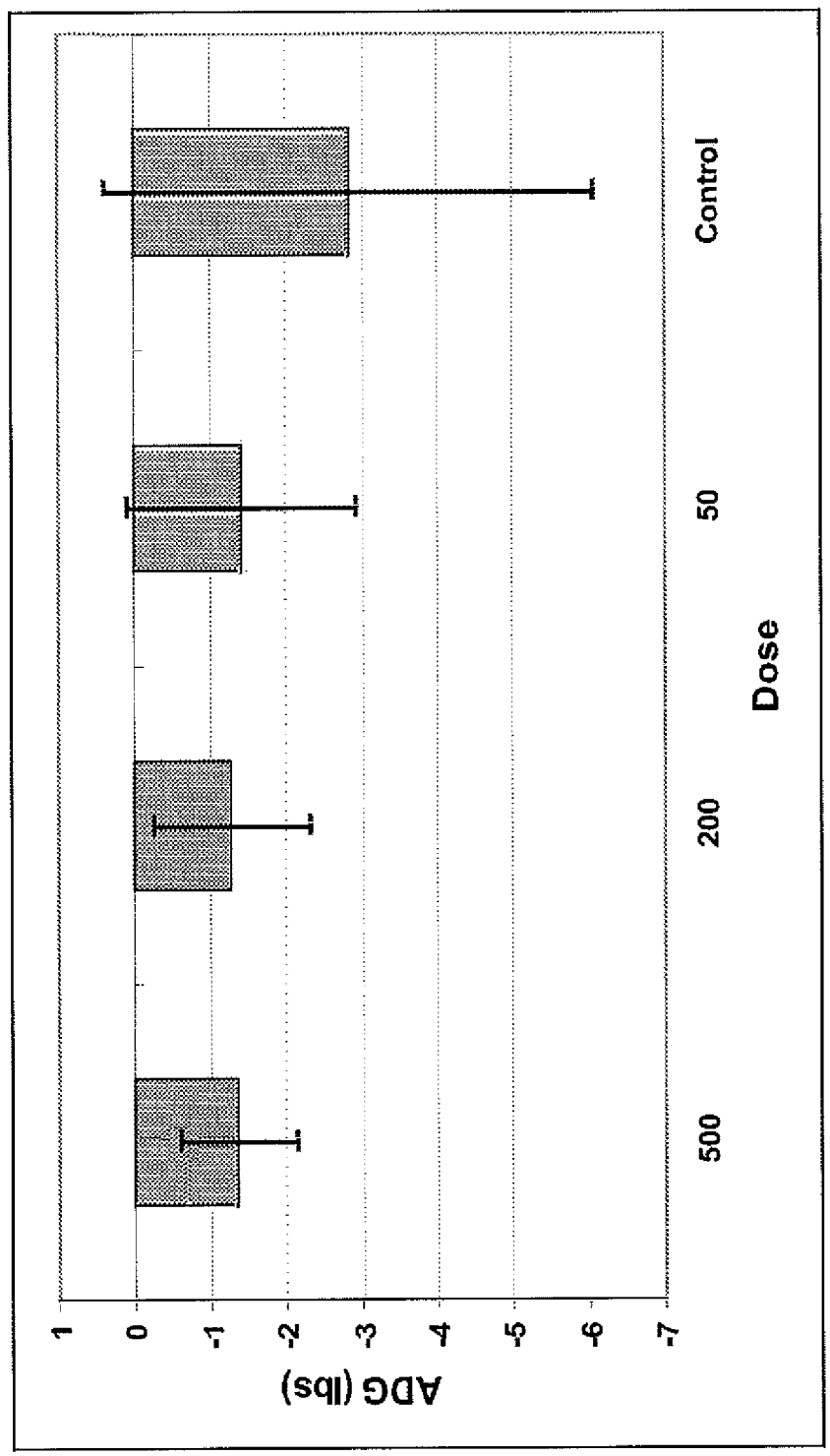
FIG. 2.2

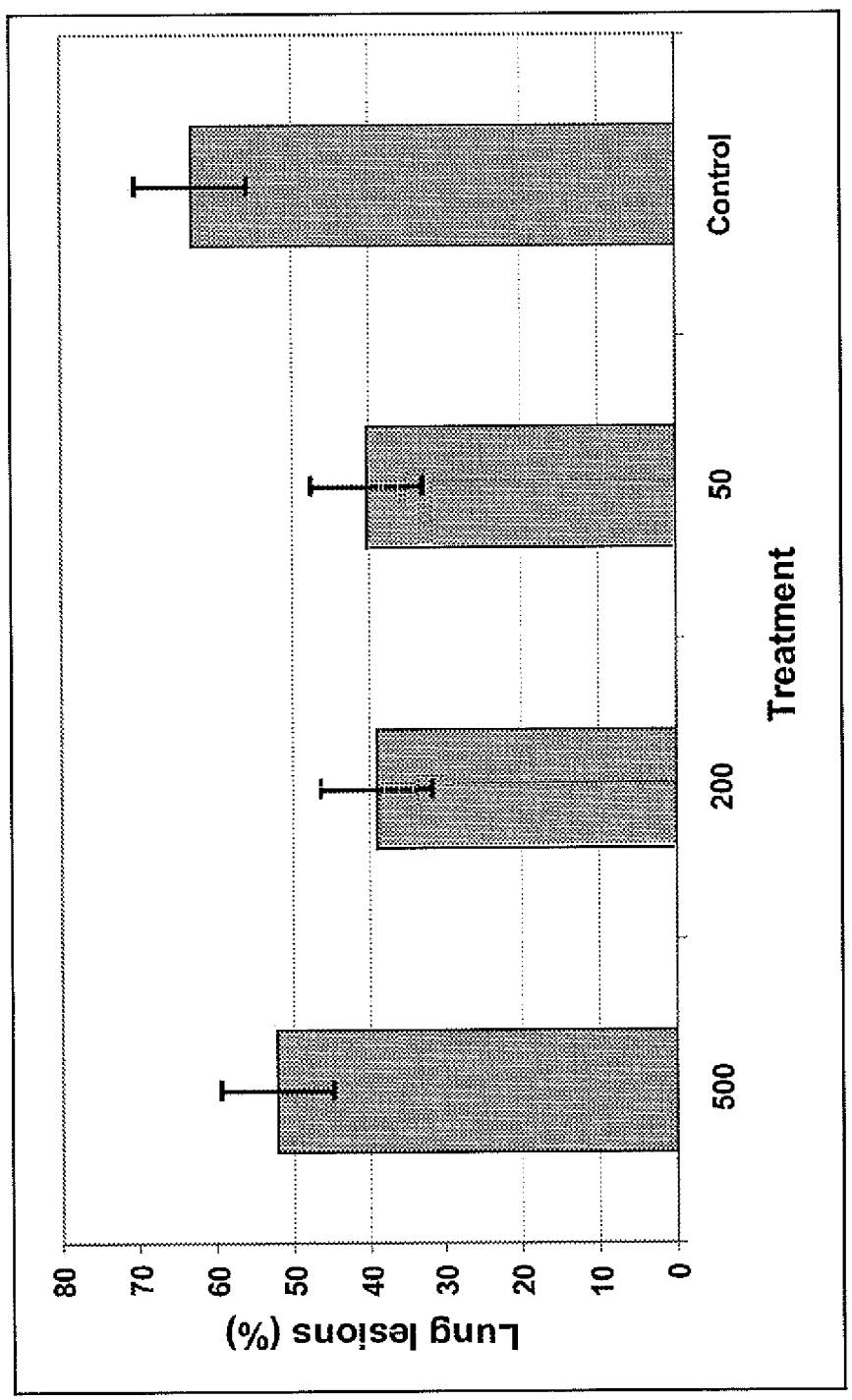
FIG. 2.3

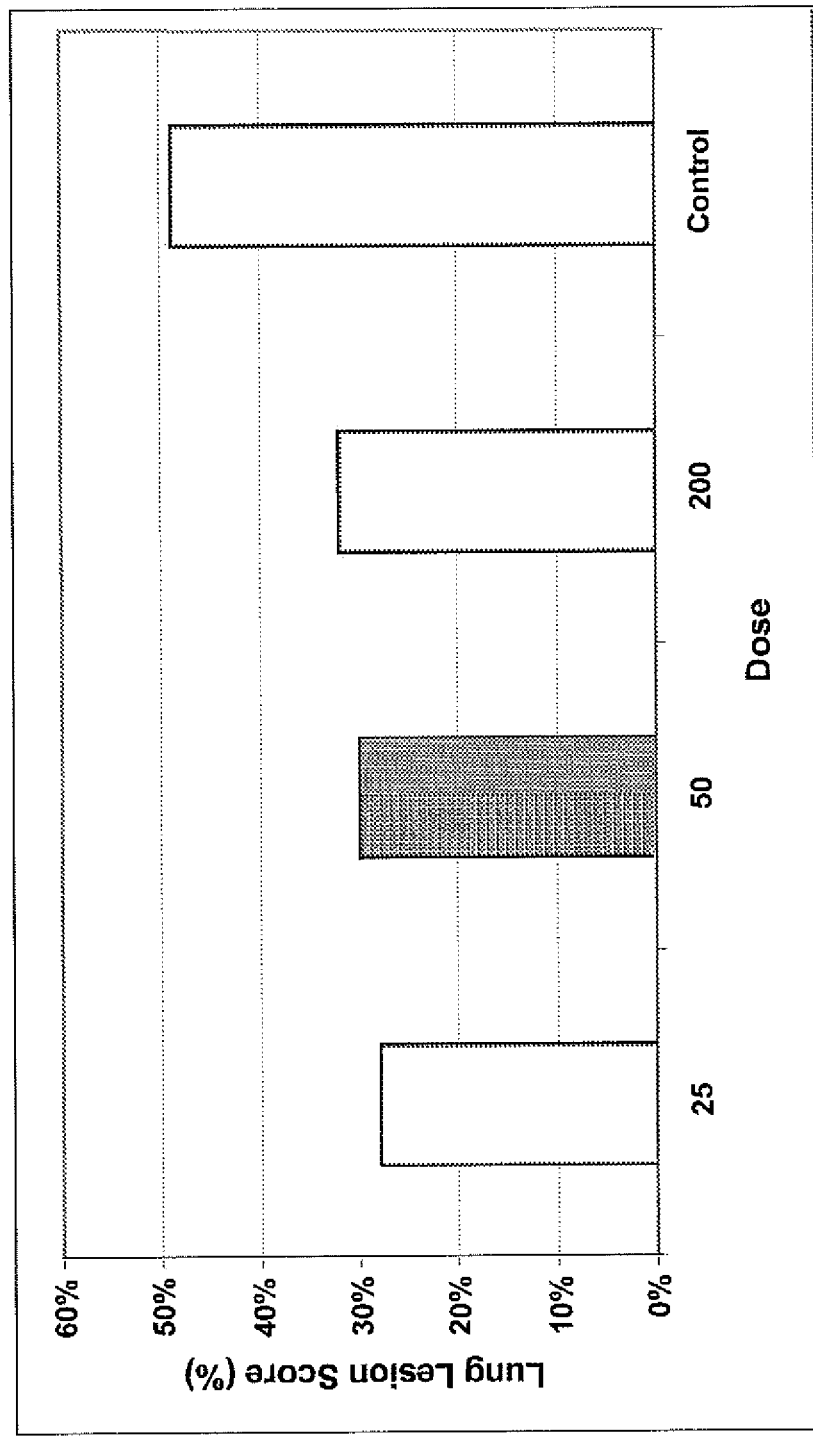
FIG. 3.1

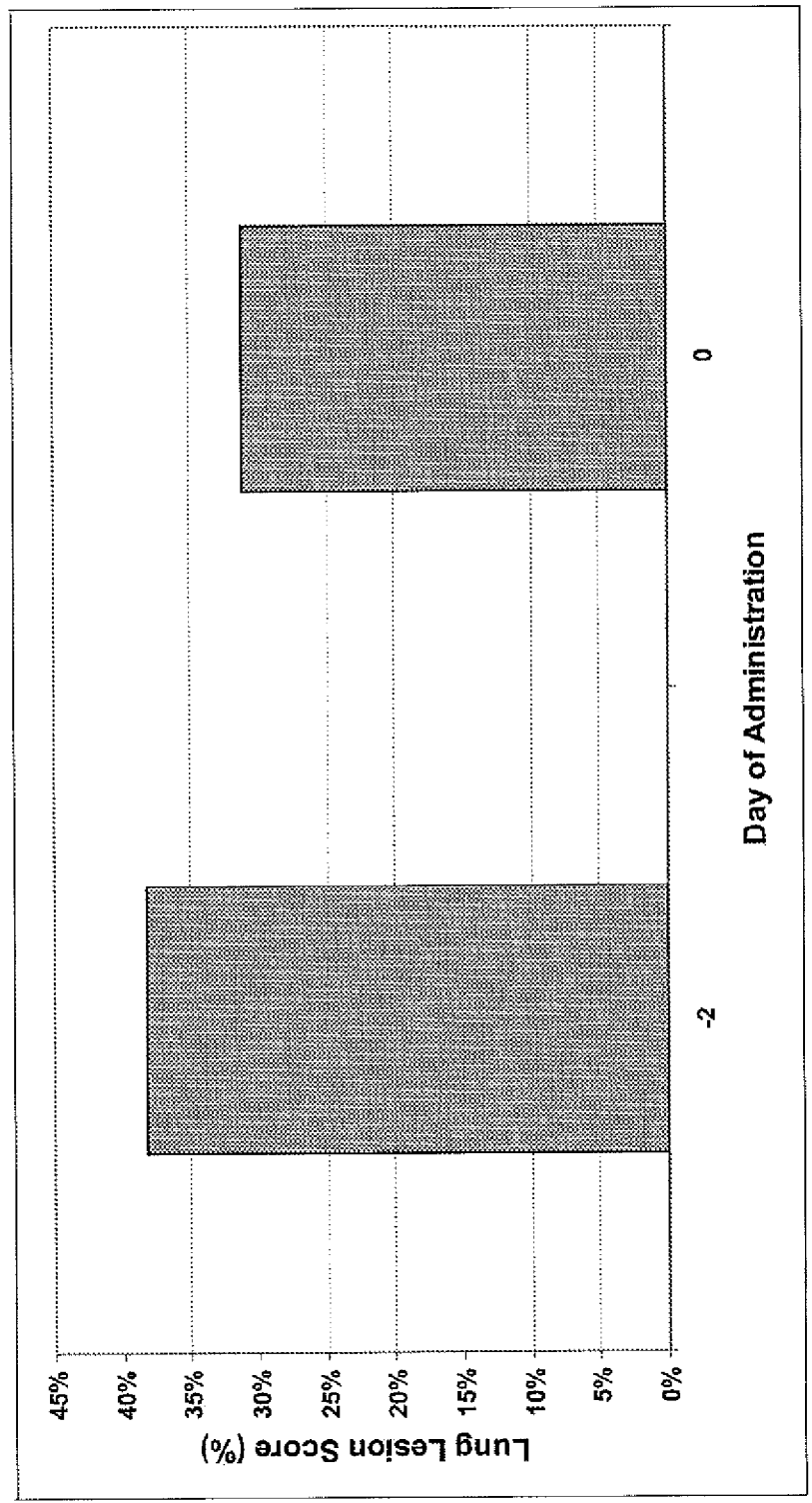
FIG. 3.2

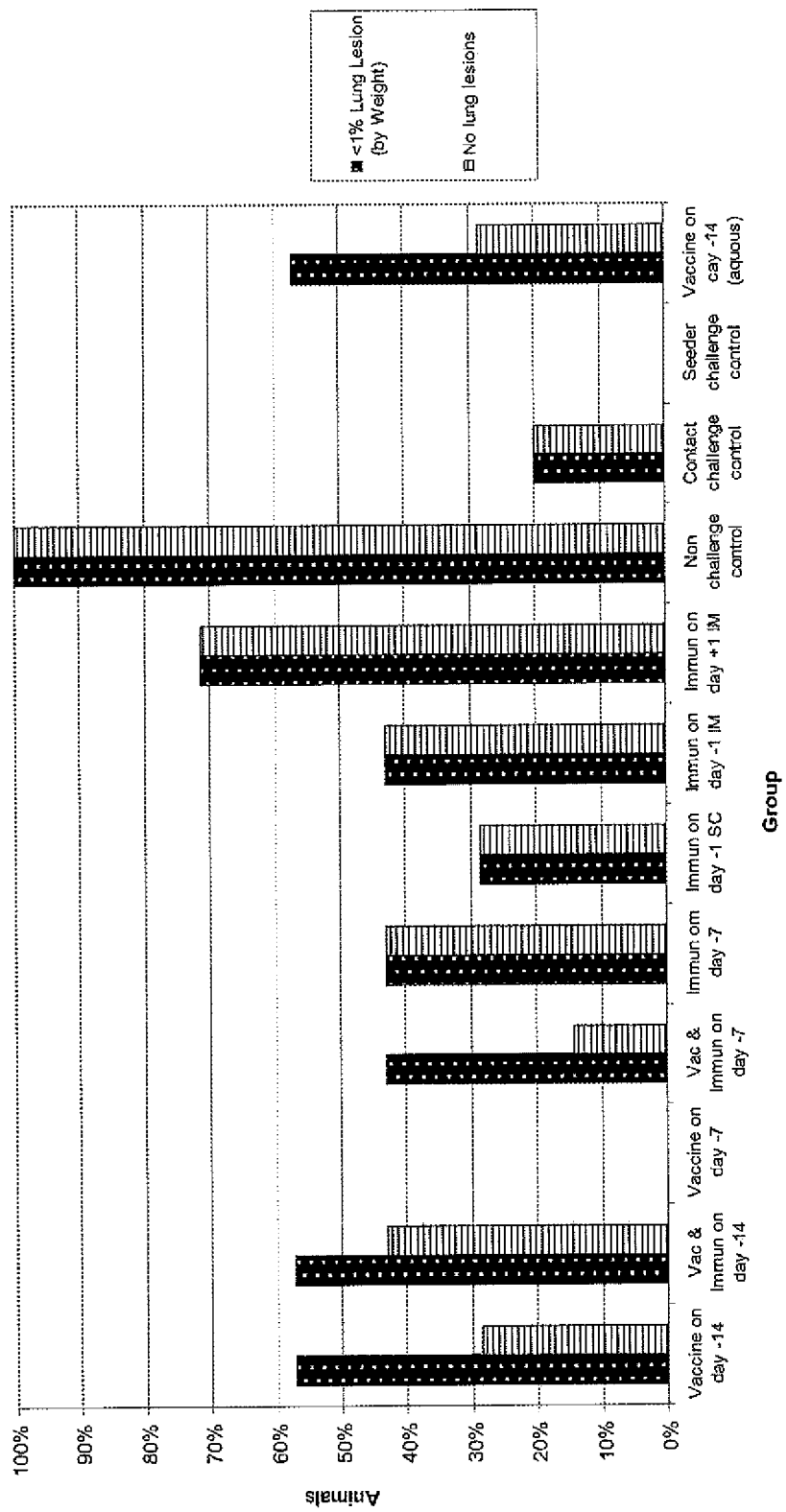
FIG. 4.1

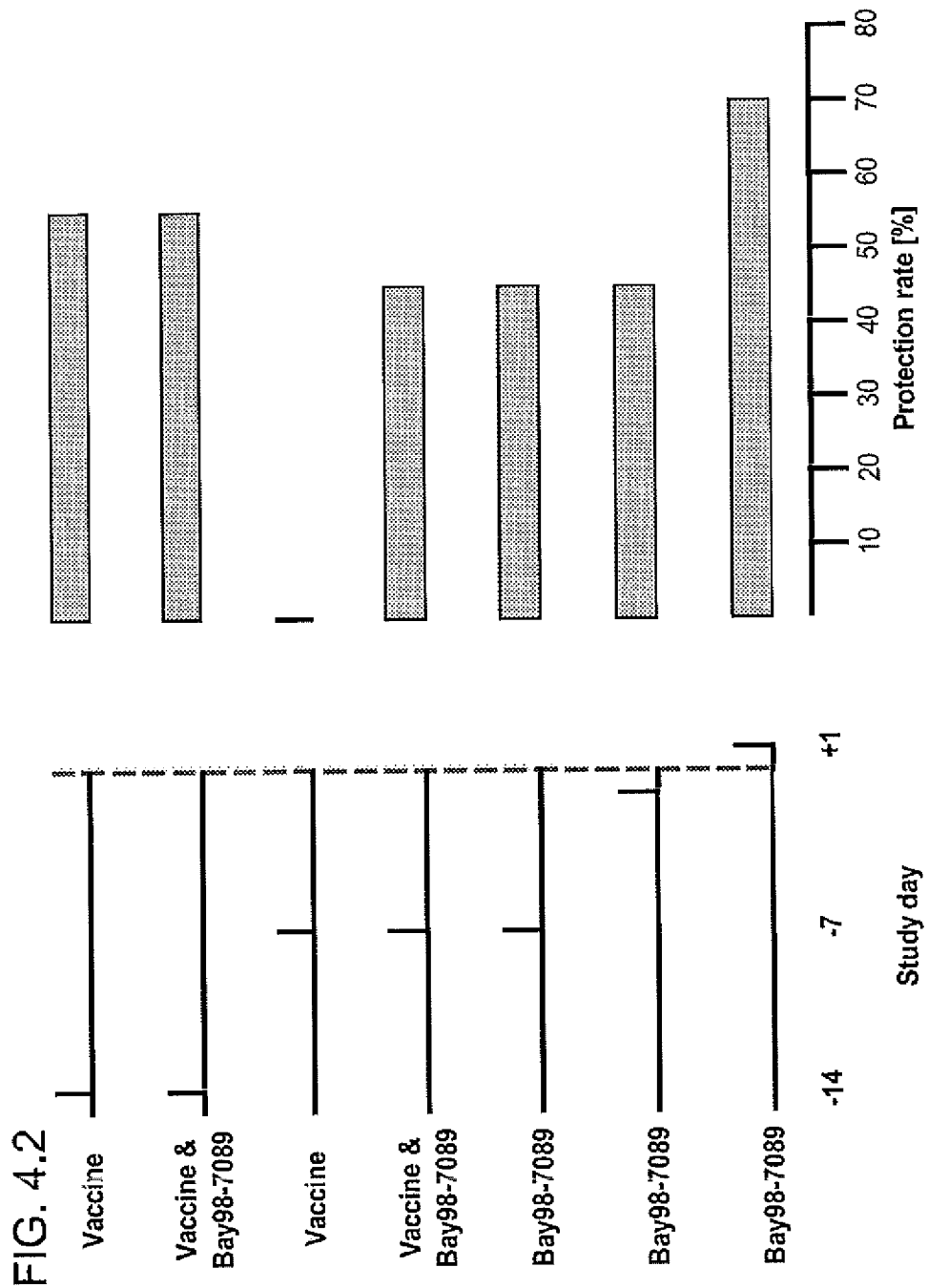

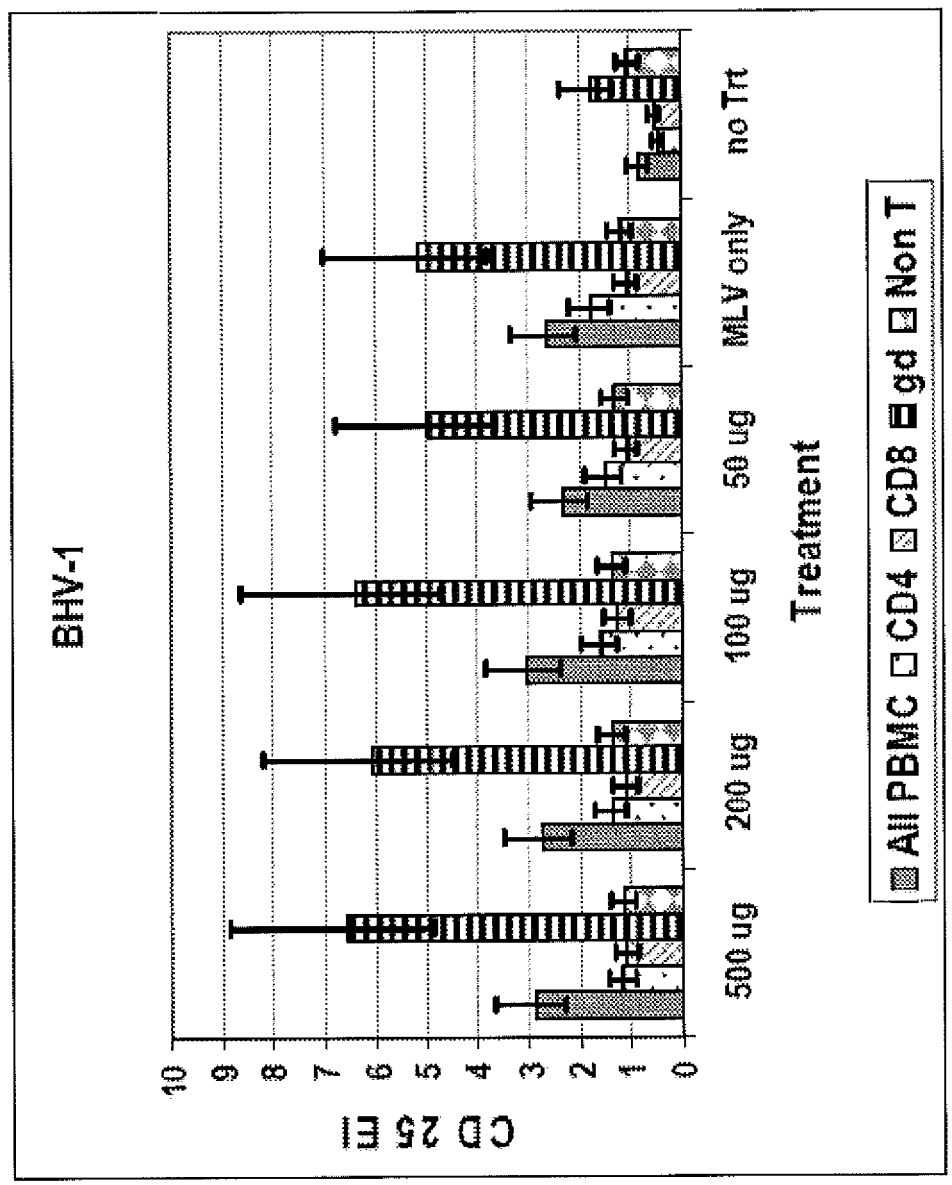
FIG. 5.1

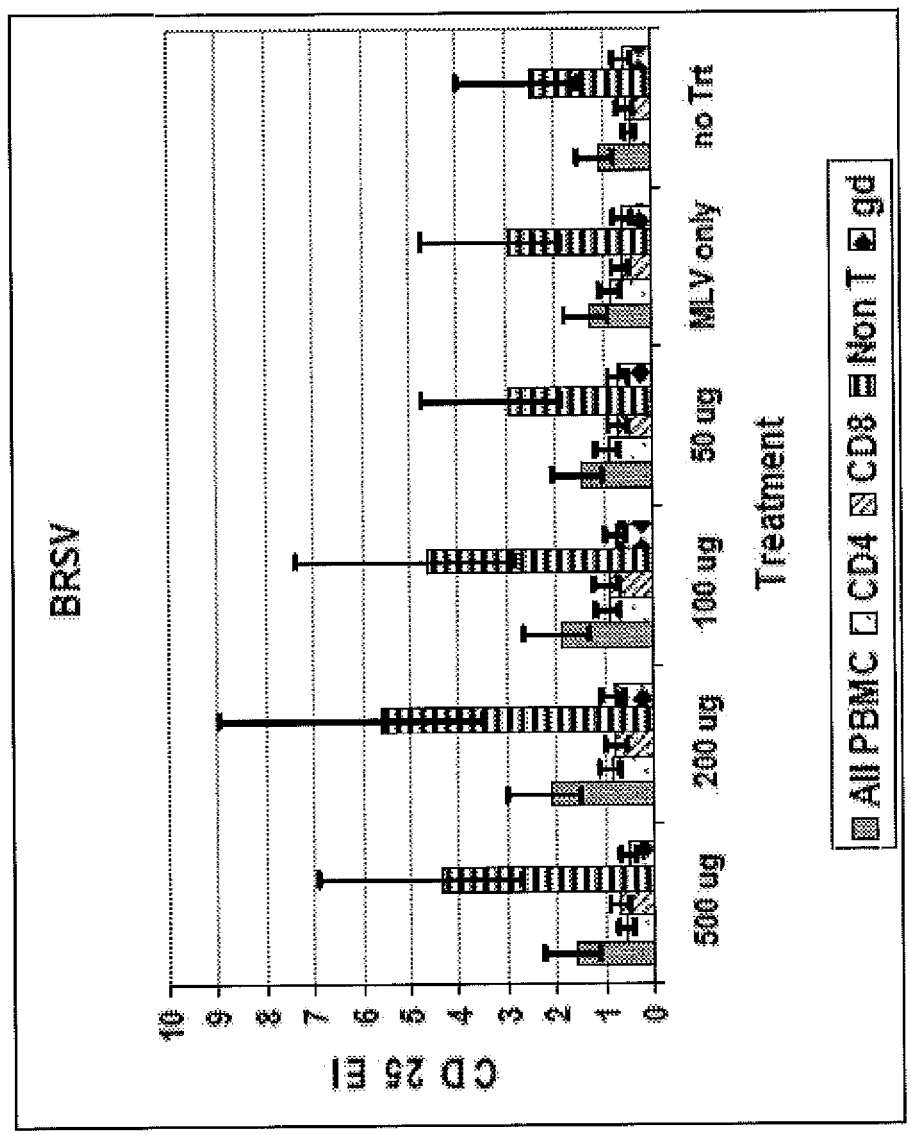
FIG. 5.2

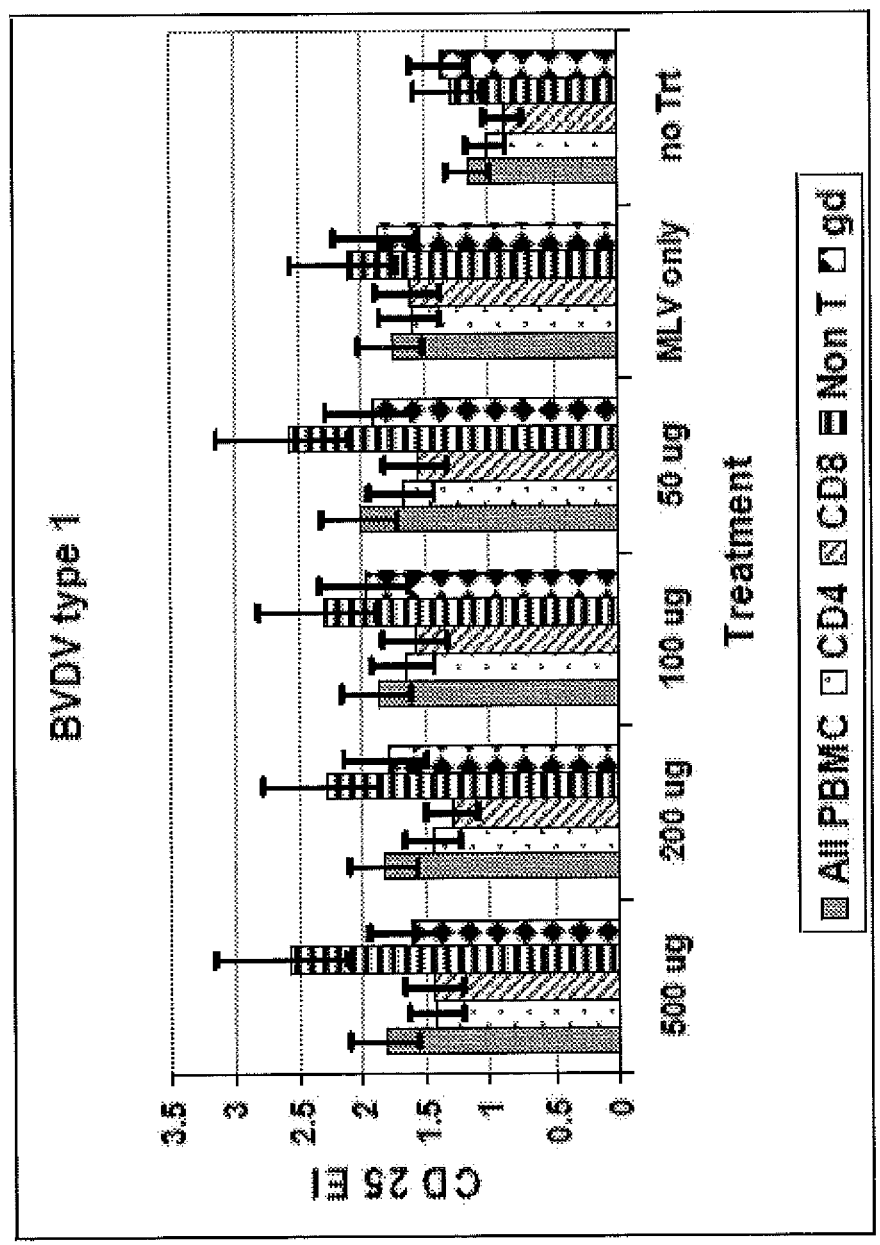
FIG. 5.3

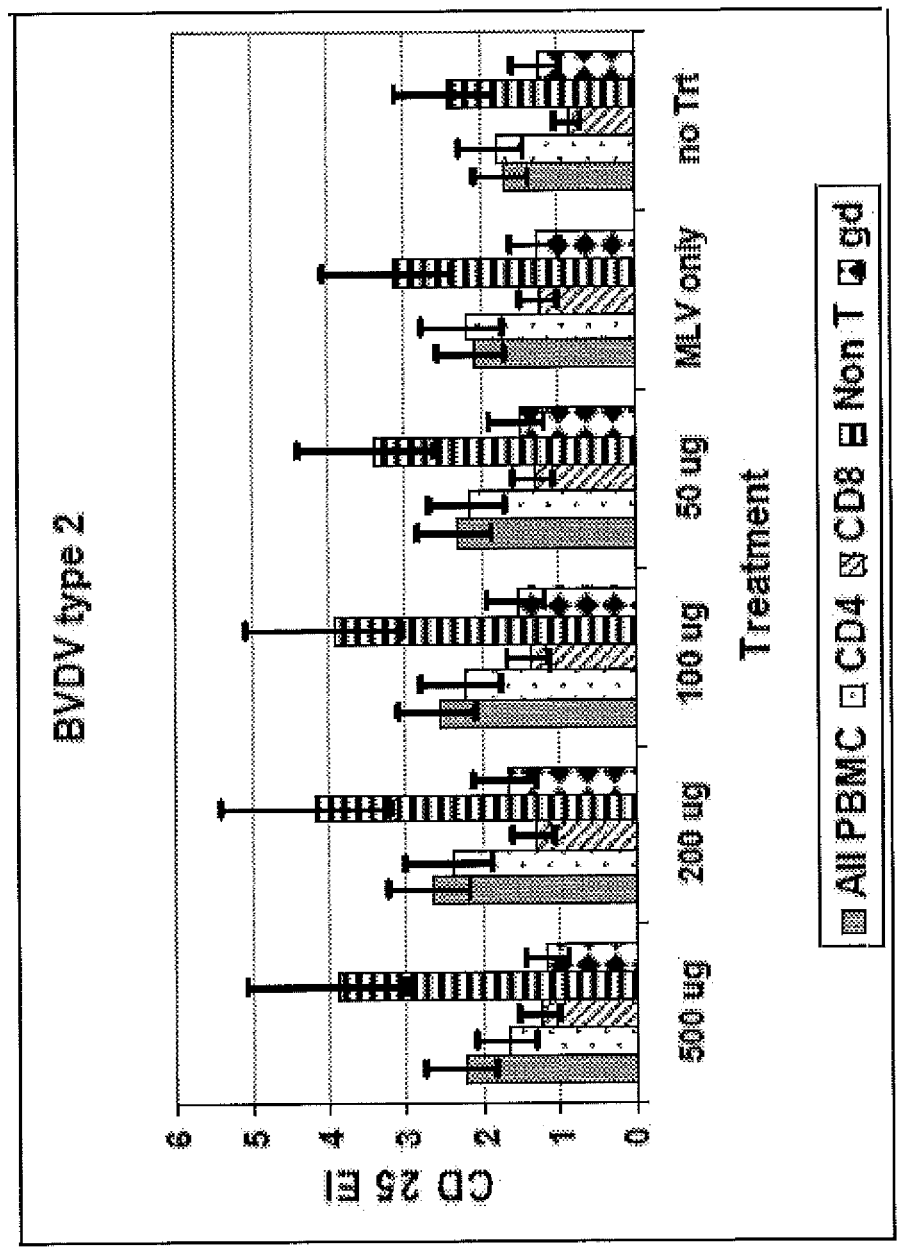
FIG. 5.4

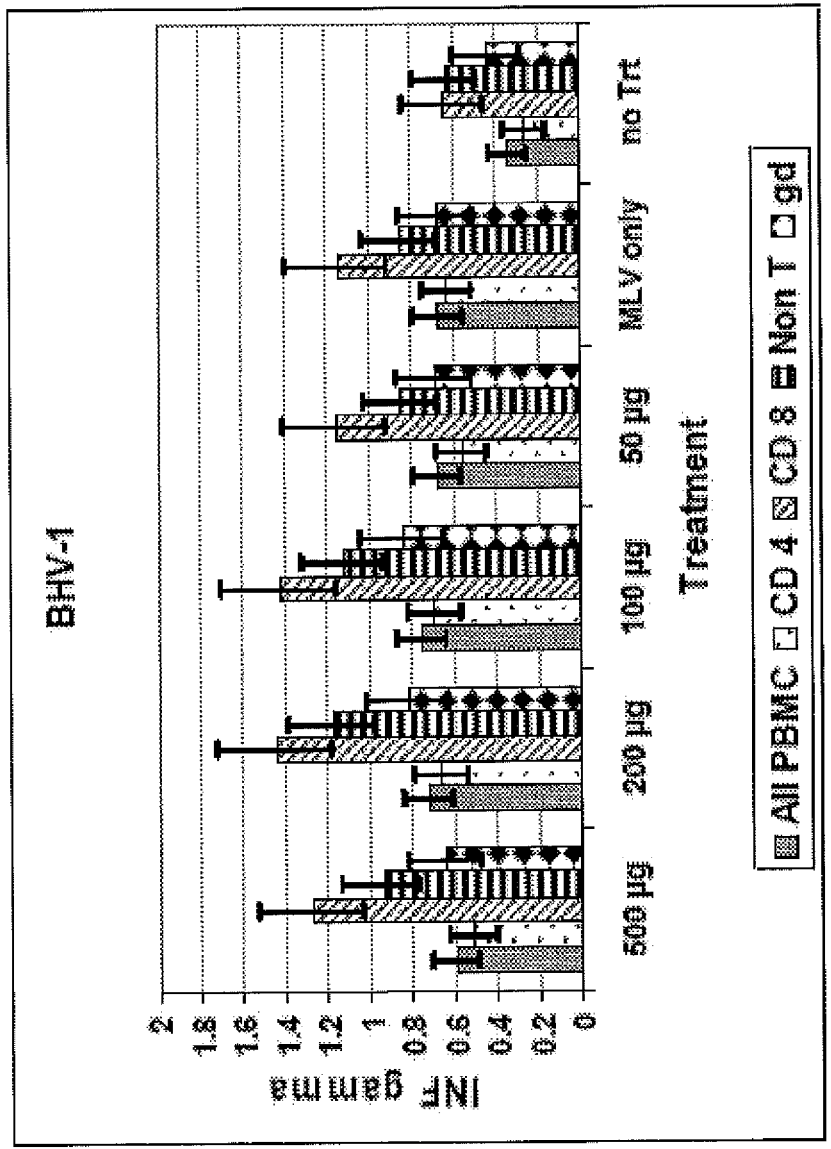
FIG. 5.5

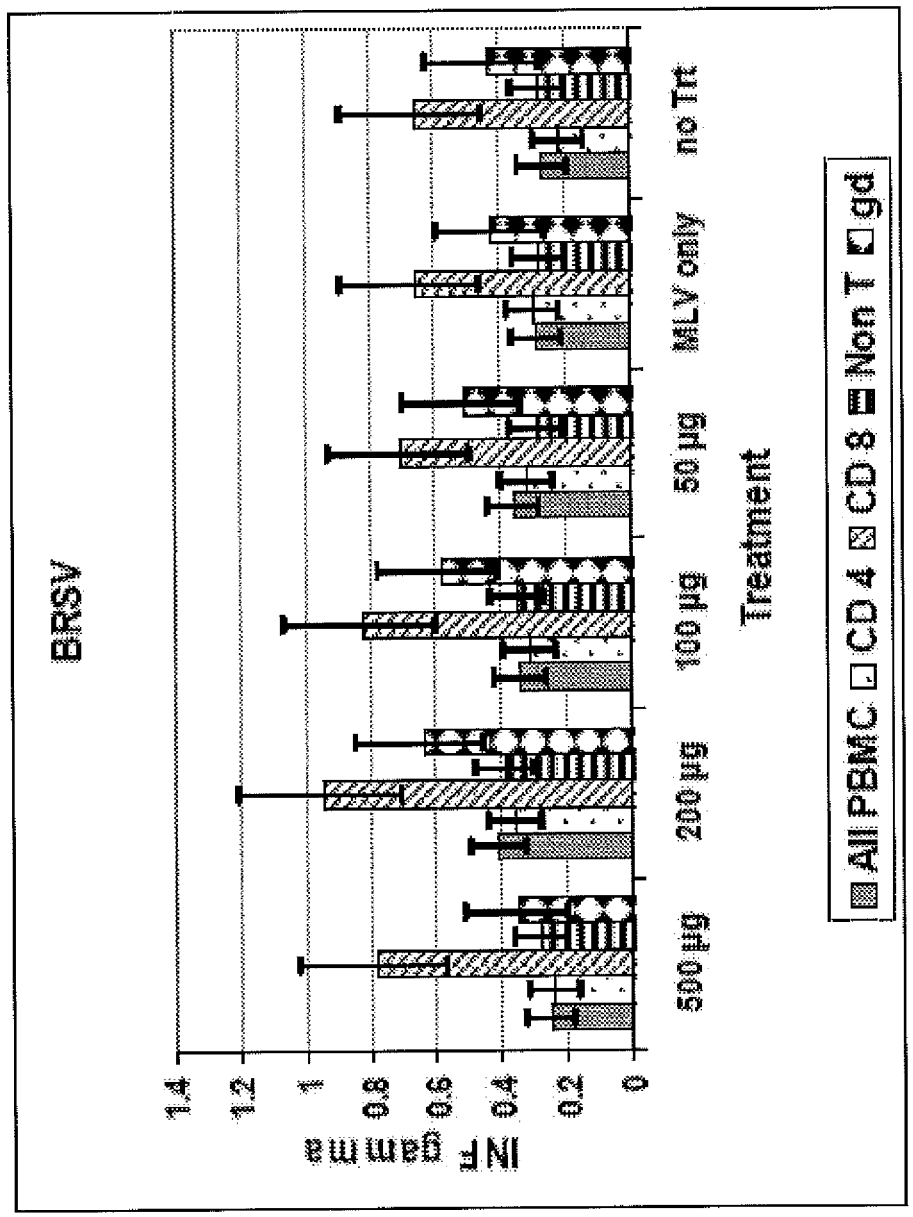
FIG. 5.6

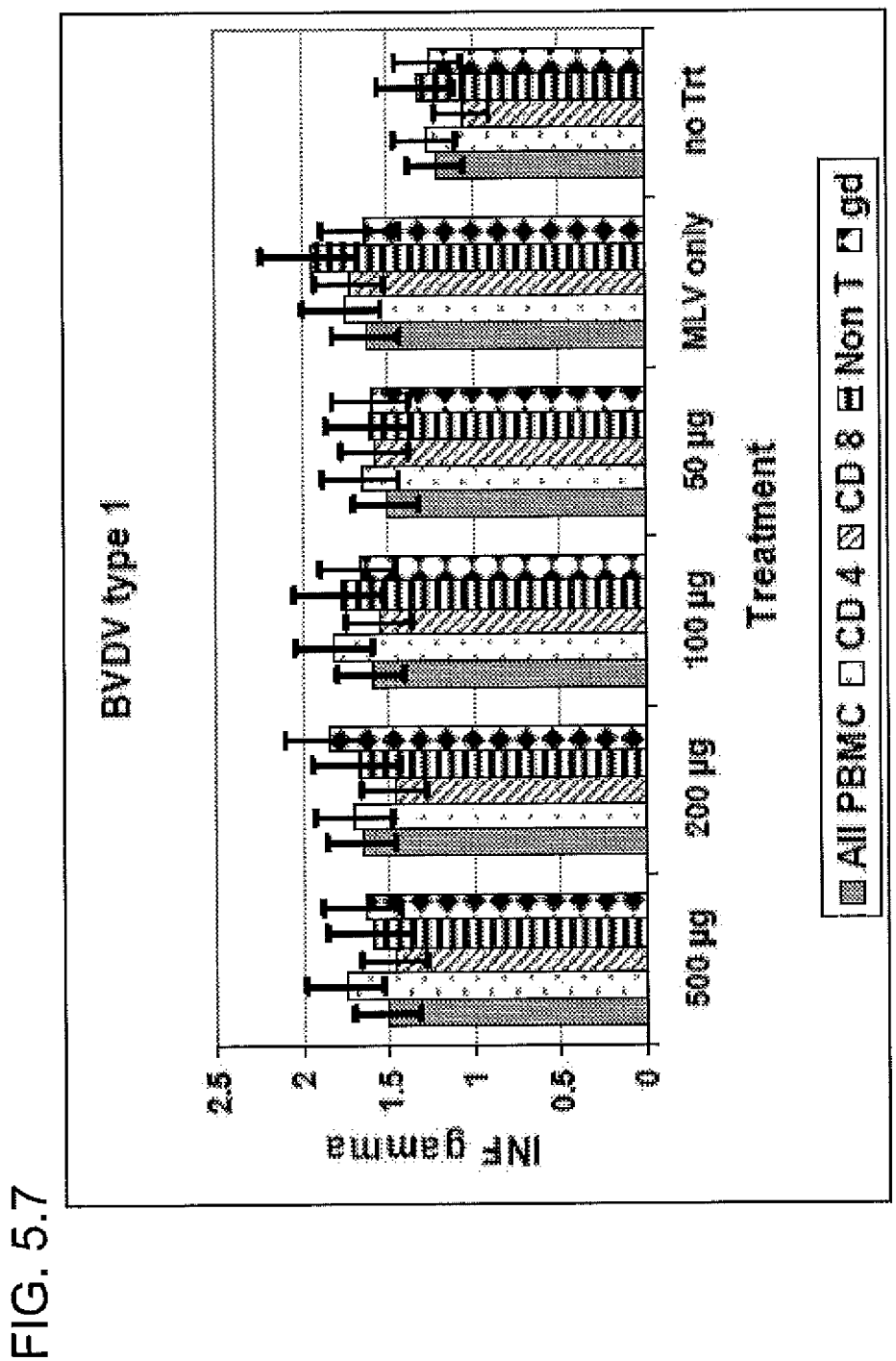
FIG. 5.7

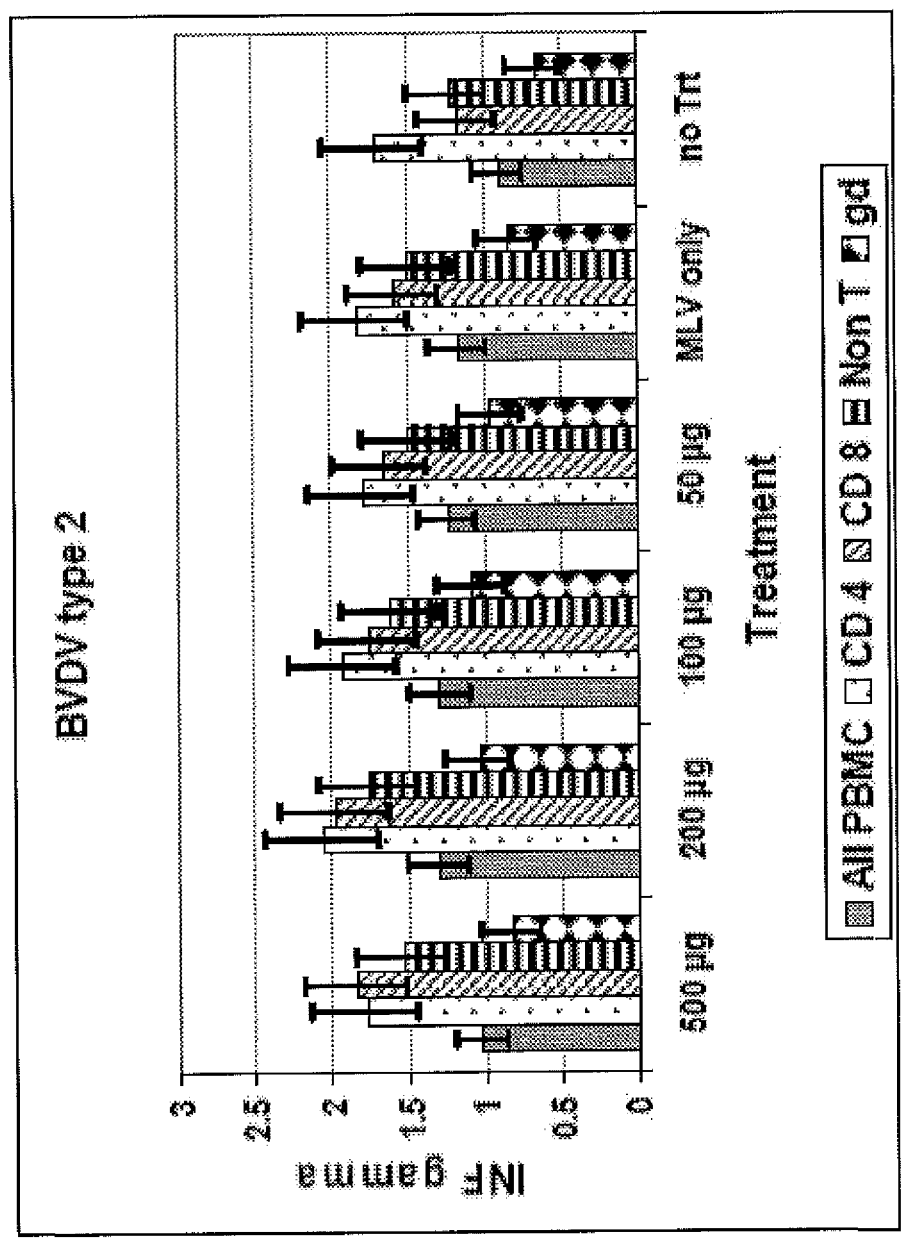
FIG. 5.8

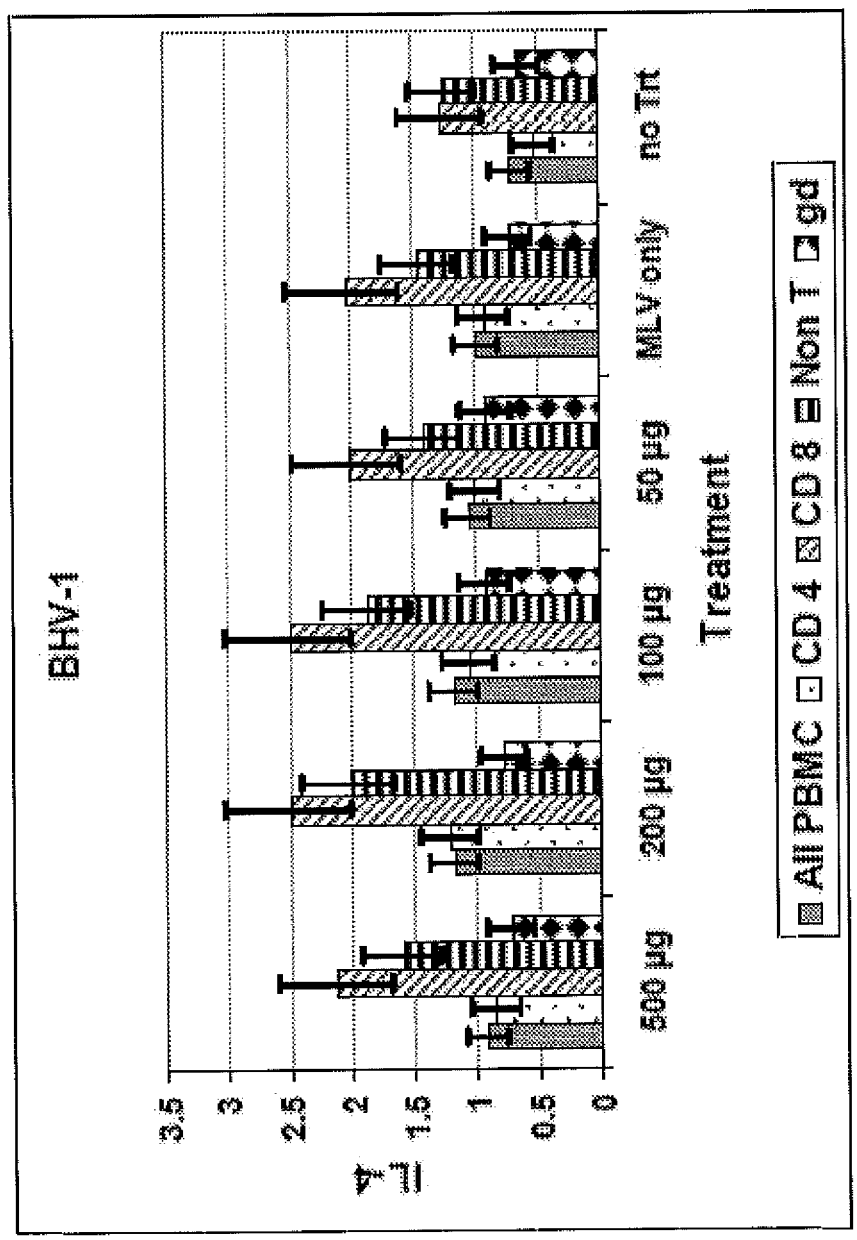
FIG. 5.9

FIG. 5.10

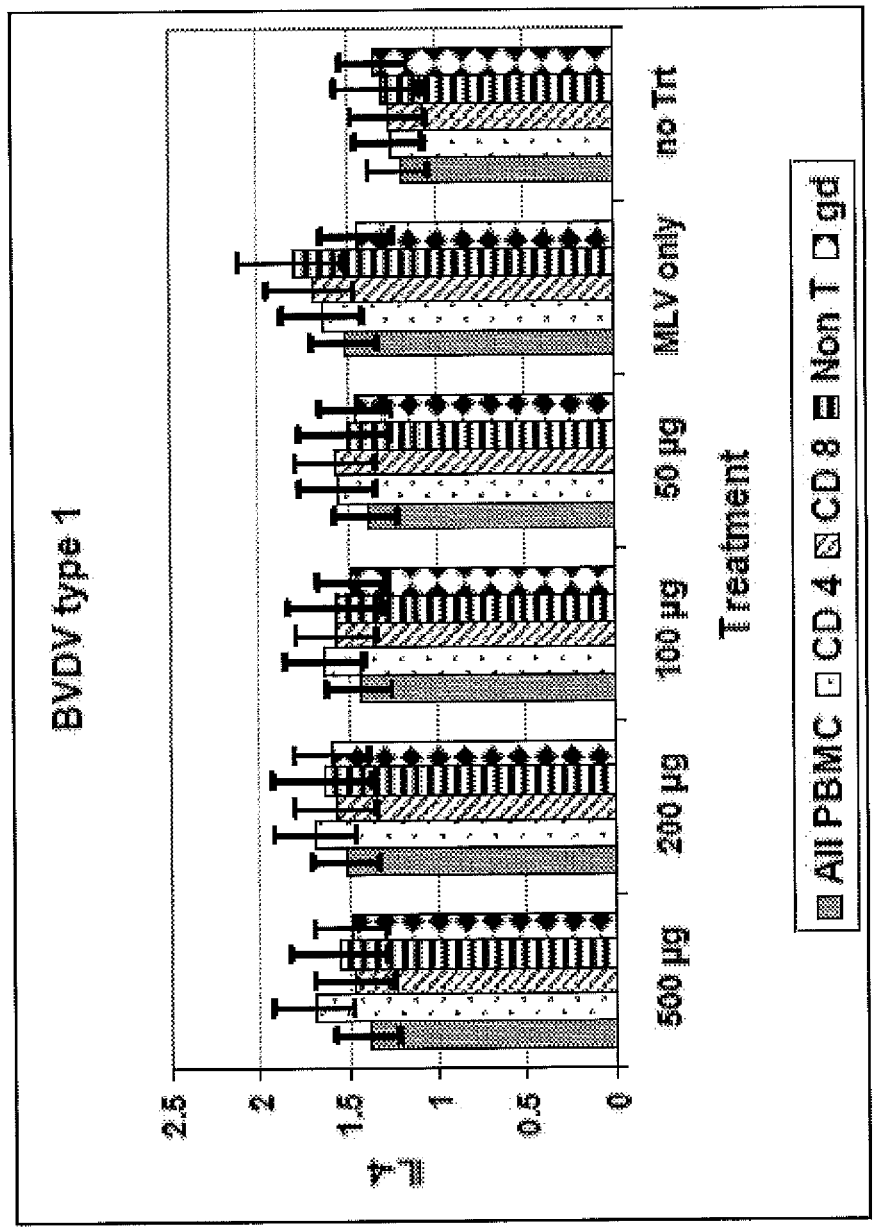
FIG. 5.11

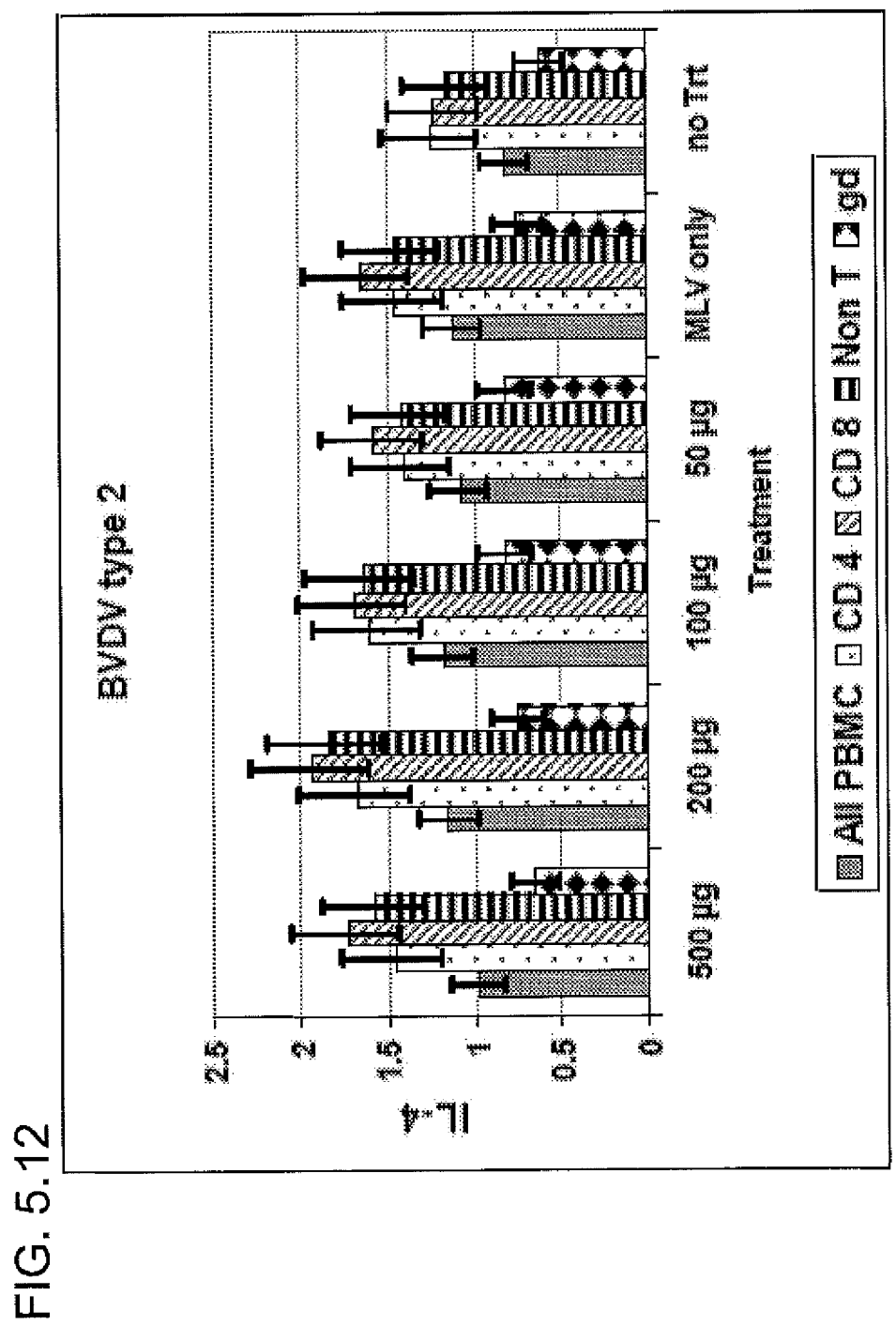
FIG. 5.12

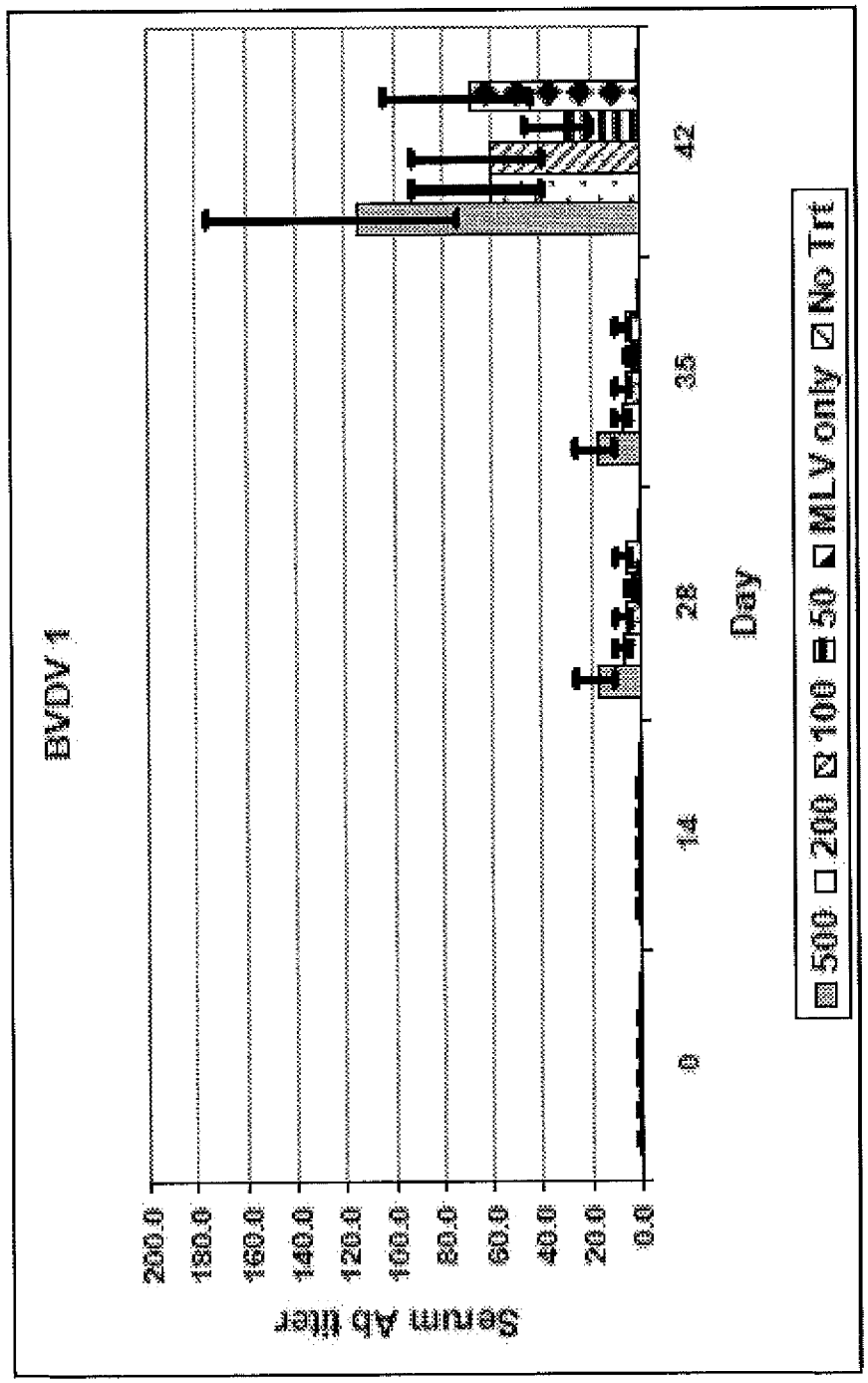
FIG. 5.13

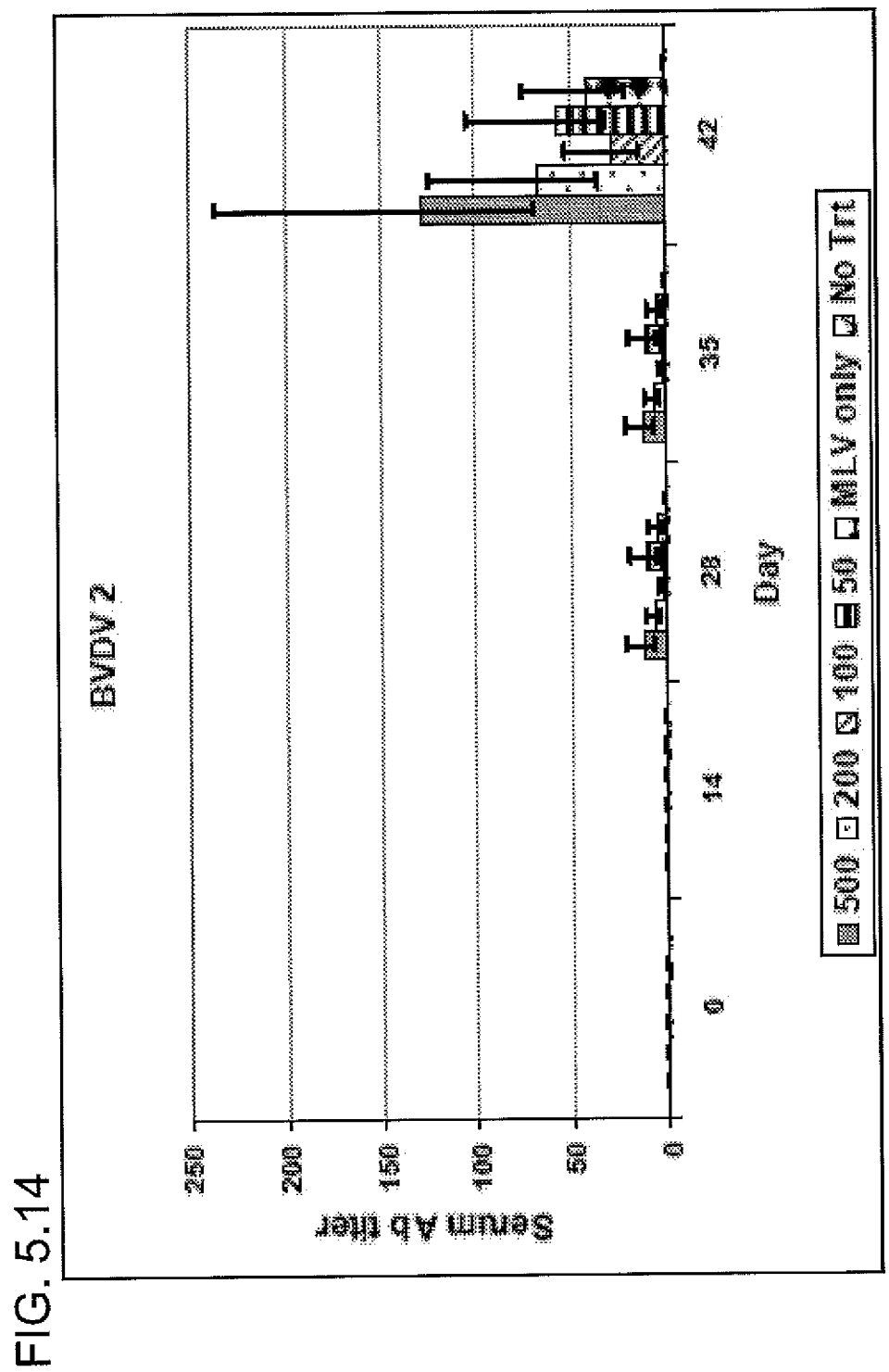
FIG. 5.14

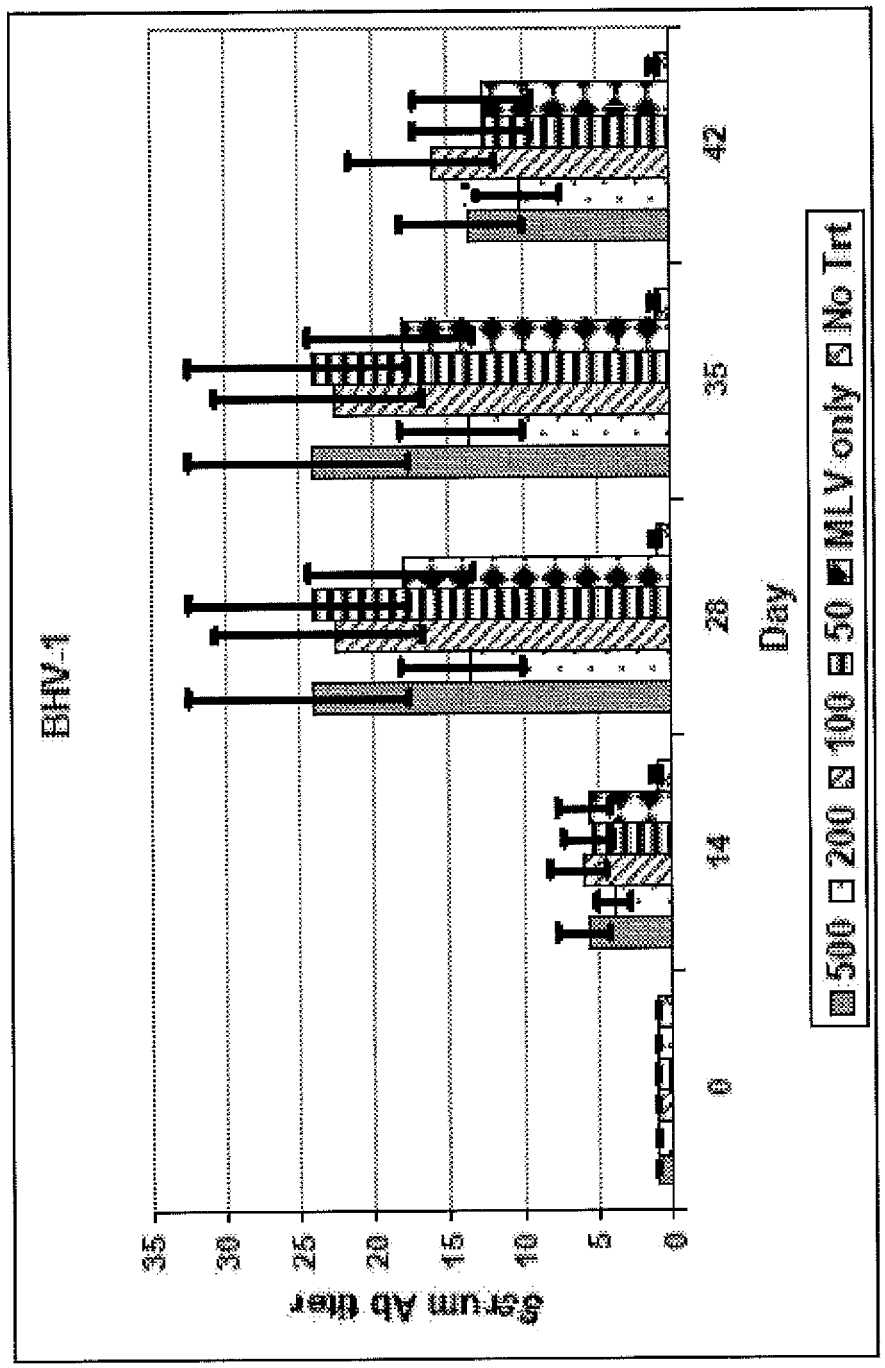
FIG. 5.15

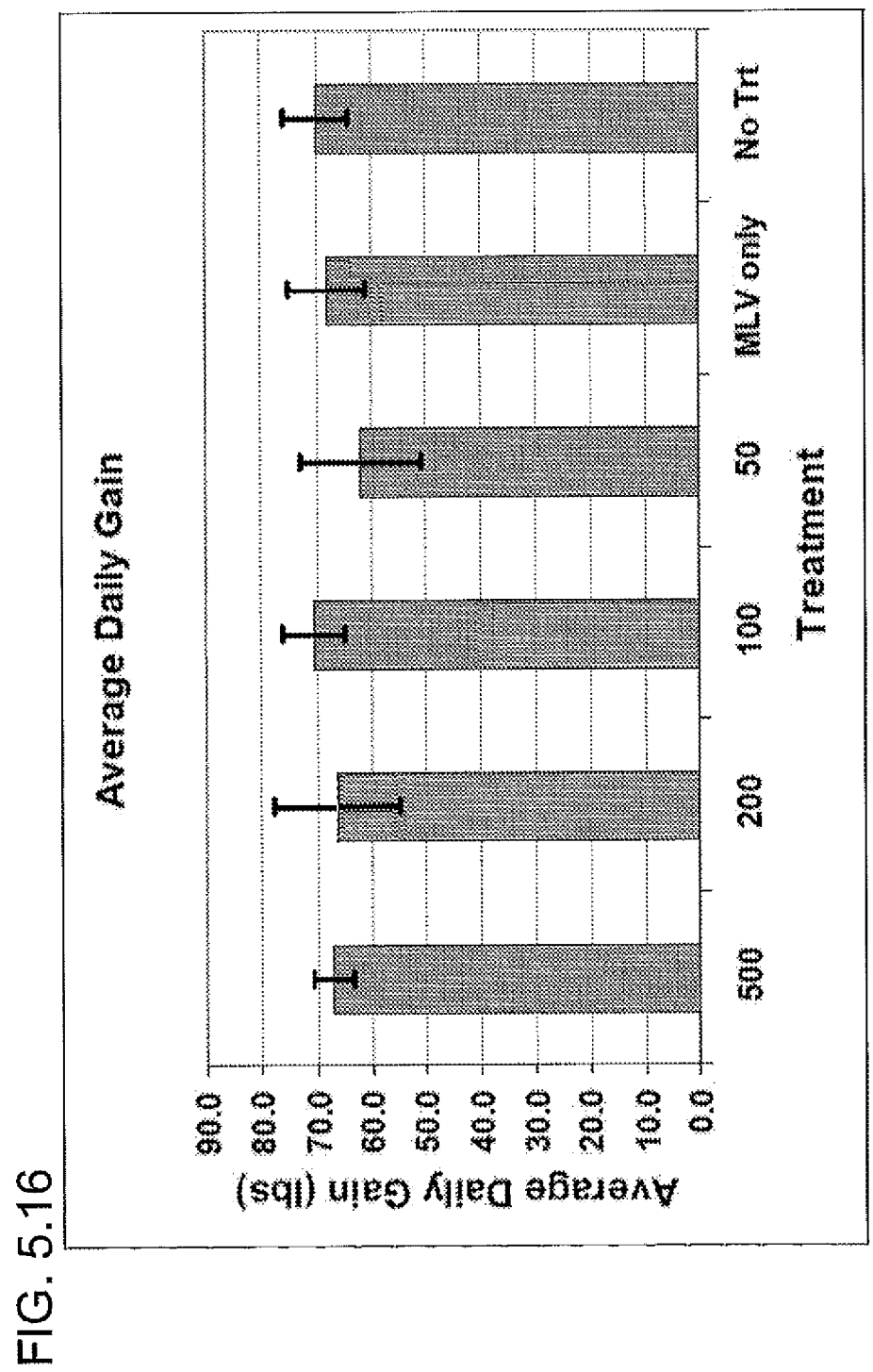
FIG. 5.16

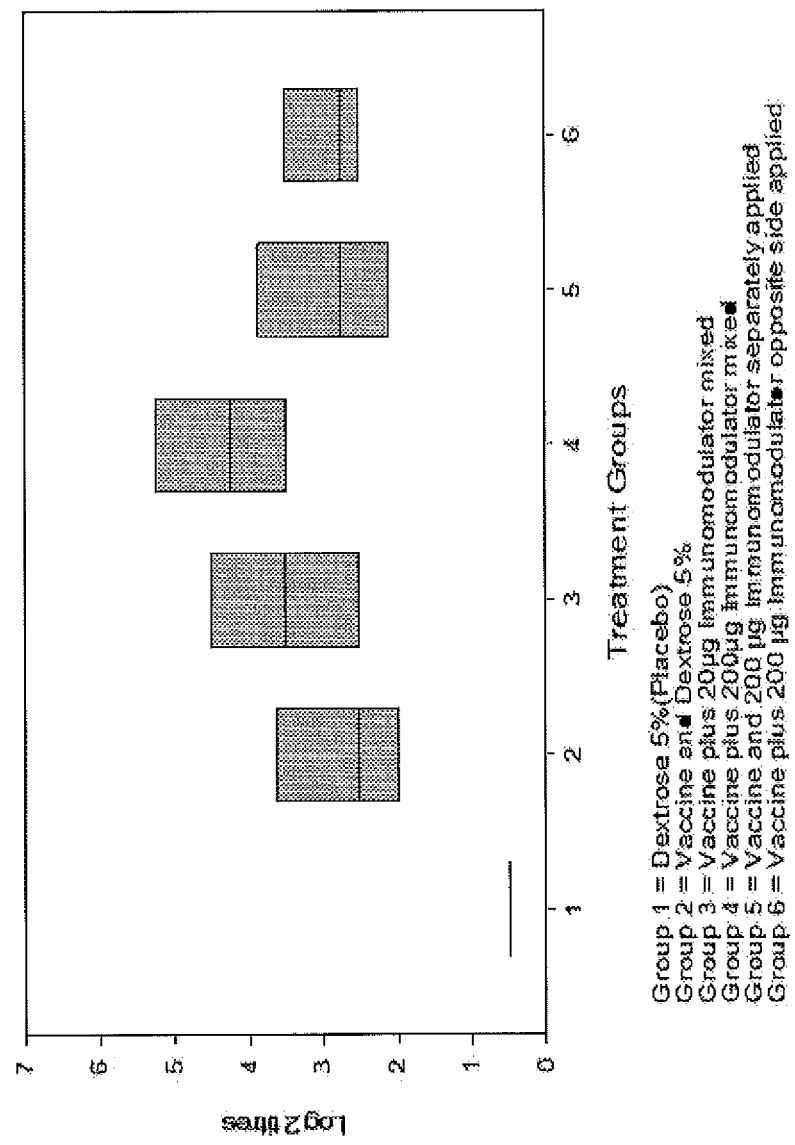
FIG. 6.1

ENHANCED IMMUNE RESPONSE IN BOVINE SPECIES

REFERENCE TO CORRESPONDING APPLICATIONS

The present application is a continuation of application Ser. No. 13/923,496 filed Jun. 21, 2013, which is a continuation of International Application No. PCT/EP2011/073414, with an international filing date of Dec. 20, 2011, and claims the benefit of Uruguayan Patent Application No. 033821, filed Dec. 20, 2011, and U.S. Provisional Patent Application Ser. No. 61/426,255, filed Dec. 22, 2010, the entire contents of which are incorporated herein by reference.

FIELD OF THE INVENTION

The present invention relates to a method of immune activation in a member of the bovine species. In particular, the present invention includes methods for eliciting systemic, non-specific and antigen-specific immune responses, which are useful for animal administration and protection against infectious disease.

BACKGROUND OF THE INVENTION

Cattle are prime targets for many types of viral, bacterial, and parasite infections. Modern production practices, such as weaning, shipment of cattle, inclement weather, and nutritional needs within the beef and dairy industries may also serve as risk factors that potentiate the incidence of disease. Bovine respiratory disease (BRD), or bovine respiratory diseases complex, as it is often referred to, occurs in both dairy and beef cattle and is one of the leading causes of economic loss to the cattle industry throughout the world. These losses are due to morbidity, mortality, reduced weight gains, treatment and prevention costs, loss of milk production, and negative impacts on carcass characteristics.

The pathogenesis of BRD is thought to arise from numerous environmental and physiological stressors, mentioned above, coupled with infectious agents. *Mannheimia* (Pasteurella) *haemolytica, Pasteurella multocida* and *Histophilus somni* (formerly Haemophilus somnus) are considered part of the normal flora of the bovine upper-respiratory tract. Conversely, the lower respiratory tract is a relatively sterile environment that is maintained by numerous immunological pathways aimed at the prevention of microbial entry. When cattle are subjected to environmental and physiological stressors, the animal's innate and acquired immune functions are compromised thereby allowing these aforementioned organisms to proliferate and subsequently colonize the lower respiratory tract. Various bovine viruses are known to have immunosuppressive effects in the lung, such as infectious bovine rhinotracheitis virus (IBRV, IBR, or BHV 1), bovine viral diarrhea virus (BVDV), bovine respiratory syncytial virus (BRSV), and parainfluenza type 3 virus (PI3). However, *Mannheimia haemolytica* is by far the most prevalent bacterial pathogen among cases of BRD.

Current prevention and treatment of BRD consists of antibiotic administration to populations of cattle upon arrival at feedlots (i.e. metaphylaxis), antibiotic therapy for sick cattle, and vaccination against BRD viruses and bacteria including *M. haemolytica*.

There are different reasons why current vaccination programs and pharmaceutical therapies are not optimal to control BRD in cattle today. First, the host defense system plays a major role in combating infectious disease in cattle. Conventional treatments include the administration of antibiotics to treat or control bacterial infections. However, there are no approved pharmaceutical treatments available against viral infections. With BRD, in most cases not only is there a bacterial infection but also a viral infection. Second, timing of vaccination is often sub-optimal. For a respiratory vaccine to be optimally effective the product should be administered 2-4 weeks prior to stress or shipment and this is typically not feasible in commercial cattle production. The vaccines are either administered too early or too late to be optimally effective.

Therefore a need exists for a method to stimulate the immune system and build an offensive response to reduce or eliminate disease causing organisms. It is important that this method is easy to administer, works alone or in combination with vaccines or helps to make such vaccines more effective, has a longer duration or that does not require added injections to maximize immunity. The present invention provides a method of eliciting a non-antigen-specific immune response in the bovine species that is easy to administer, works alone or in combination with vaccines, induces a protective response against one or more infectious agents.

BRIEF DESCRIPTION OF THE DRAWINGS

FIG. 1.1 graphically depicts average rectal temperature data according to dose of immunomodulator administered as described in Example 1.

FIG. 1.2 graphically depicts average daily weight gain data according to dose of immunomodulator administered as described in Example 1.

FIG. 1.3 graphically depicts the model-adjusted lung lesion scores with respect to dose of immunomodulator administered as described in Example 1.

FIG. 2.1 graphically depicts average rectal temperature data according to dose of immunomodulator administered as described in Example 2.

FIG. 2.2 graphically depicts average daily weight gain data according to dose of immunomodulator administered as described in Example 2.

FIG. 2.3 graphically depicts the model-adjusted lung lesion scores with respect to dose of immunomodulator administered as described in Example 2.

FIG. 3.1 graphically depicts the model-adjusted lung lesion scores with respect to dose of immunomodulator administered as described in Example 3

FIG. 3.2 graphically depicts the model-adjusted lung lesion scores with respect to day of immunomodulator administration as described in Example 3.

FIG. 4.1 graphically depicts % of protected animals by treatment group as described in Example 4.

FIG. 4.2 graphically depicts percent of animals protected by treatment group (<1% lung lesions and no lung lesions) as described in Example 4.

FIG. 5.1 graphically depicts measurements of the CD 25 E1 expression index (y-axis) in cells infected with BHV-1 across all five cell types for each of the 6 treatment groups (x-axis) as described in Example 5.

FIG. 5.2 graphically depicts measurements of the CD 25 E1 expression index (y-axis) in cells infected with BRSV across all five cell types for each of the 6 treatment groups (x-axis) as described in Example 5.

FIG. 5.3 graphically depicts measurements of the CD 25 E1 expression index (y-axis) in cells infected with BVDV type 1 across all five cell types for each of the 6 treatment groups (x-axis) as described in Example 5.

FIG. 5.4 graphically depicts measurements of the CD 25 E1 expression index (y-axis) in cells infected with BVDV type 2 across all five cell types for each of the 6 treatment groups (x-axis) as described in Example 5.

FIG. 5.5 graphically depicts measurements of the IFNγ expression index (y-axis) in cells infected with BHV-1 across all five cell types for each of the 6 treatment groups (x-axis) as described in Example 5.

FIG. 5.6 graphically depicts measurements of the IFNγ expression index (y-axis) in cells infected with BRSV across all five cell types for each of the 6 treatment groups (x-axis) as described in Example 5.

FIG. 5.7 graphically depicts measurements of the IFNγ expression index (y-axis) in cells infected with BVDV type 1 across all five cell types for each of the 6 treatment groups (x-axis) as described in Example 5.

FIG. 5.8 graphically depicts measurements of the IFNγ expression index (y-axis) in cells infected with BVDV type 2 across all five cell types for each of the 6 treatment groups (x-axis) as described in Example 5.

FIG. 5.9 graphically depicts measurements of the IL-4 expression index (y-axis) in cells infected with BHV-1 across all five cell types for each of the 6 treatment groups (x-axis) as described in Example 5.

FIG. 5.10 graphically depicts measurements of the IL-4 expression index (y-axis) in cells infected with BRSV across all five cell types for each of the 6 treatment groups (x-axis) as described in Example 5.

FIG. 5.11 graphically depicts measurements of the IL-4 expression index (y-axis) in cells infected with BVDV type 1 across all five cell types for each of the 6 treatment groups (x-axis) as described in Example 5.

FIG. 5.12 graphically depicts measurements of the IL-4 expression index (y-axis) in cells infected with BVDV type 2 across all five cell types for each of the 6 treatment groups (x-axis) as described in Example 5.

FIG. 5.13 graphically depicts Model adjusted serum antibody titer estimates (y-axis) in cells infected with BVDV type 1 across all five cell types for each of the 6 treatment groups (x-axis) as described in Example 5.

FIG. 5.14 graphically depicts Model adjusted serum antibody titer estimates (y-axis) in cells infected with BVDV type 2 across all five cell types for each of the 6 treatment groups (x-axis) as described in Example 5.

FIG. 5.15 graphically depicts Model adjusted serum antibody titer estimates (y-axis) in cells infected with BHV-1 across all five cell types for each of the 6 treatment groups (x-axis) as described in Example 5.

FIG. 5.16 graphically depicts model-adjusted average daily gain outcomes as described in Example 5.

FIG. 6.1 graphically depicts the BHV1 SNT titers for the treatment groups as described in Example 6.

DETAILED DESCRIPTION OF THE INVENTION

The method of eliciting an immune response in a member of the bovine species of the present invention includes administering to the member of the bovine species an effective amount of an immunomodulator composition to elicit an immune response. The immunomodulator composition includes a liposome delivery vehicle and at least one nucleic acid molecule. In addition, the immunomodulator elicits a non-antigen-specific immune response that is effective alone or enhances the operation of at least one biological agent such as a vaccine, when administered prior to such a vaccine, co-administered with such a vaccine, administered post vaccination, or mixed with the vaccine.

The methods provide new treatment strategies for protecting the bovine species from infectious diseases and treating populations having infectious disease. Finally, the method of the present invention provides a more rapid, a longer and better protection against a disease when the immunomodulator is used in combination with a vaccine.

1. Composition a. Immunomodulator

In one embodiment of the invention, the immunomodulator composition includes a liposome delivery vehicle and at least one nucleic acid molecule, as described in U.S. Pat. No. 6,693,086, and incorporated herein by reference.

A suitable liposome delivery vehicle comprises a lipid composition that is capable of delivering nucleic acid molecules to the tissues of the treated subject. A liposome delivery vehicle is preferably capable of remaining stable in a subject for a sufficient amount of time to deliver a nucleic acid molecule and/or a biological agent. In one embodiment, the liposome delivery vehicle is stable in the recipient subject for at least about 5 minutes. In another embodiment, the liposome delivery vehicle is stable in the recipient subject for at least about 1 hour. In yet another embodiment, the liposome delivery vehicle is stable in the recipient subject for at least about 24 hours.

A liposome delivery vehicle of the present invention comprises a lipid composition that is capable of fusing with the plasma membrane of a cell to deliver a nucleic acid molecule into a cell. In one embodiment, when delivered a nucleic acid: liposome complex of the present invention is at least about 1 picogram (pg) of protein expressed per milligram (mg) of total tissue protein per microgram (µg) of nucleic acid delivered. In another embodiment, the transfection efficiency of a nucleic acid: liposome complex is at least about 10 pg of protein expressed per mg of total tissue protein per µg of nucleic acid delivered; and in yet another embodiment, at least about 50 pg of protein expressed per mg of total tissue protein per µg of nucleic acid delivered. The transfection efficiency of the complex may be as low as 1 femtogram (fg) of protein expressed per mg of total tissue protein per µg of nucleic acid delivered, with the above amounts being more preferred.

A preferred liposome delivery vehicle of the present invention is between about 100 and 500 nanometers (nm), in another embodiment, between about 150 and 450 nm and in yet another embodiment, between about 200 and 400 nm in diameter.

Suitable liposomes include any liposome, such as those commonly used in, for example, gene delivery methods known to those of skill in the art. Preferred liposome delivery vehicles comprise multilamellar vesicle (MLV) lipids and extruded lipids. Methods for preparation of MLV's are well known in the art. More preferred liposome delivery vehicles comprise liposomes having a polycationic lipid composition (i.e., cationic liposomes) and/or liposomes having a cholesterol backbone conjugated to polyethylene glycol. Exemplary cationic liposome compositions include, but are not limited to, N-[1-(2,3-dioleyloxy)propyl]-N,N,N-trimethylammonium chloride (DOTMA) and cholesterol, N-[1-(2,3-dioleoyloxy)propyl]-N,N,N-trimethylammonium chloride (DOTAP) and cholesterol, 1-[2-(oleoyloxy)ethyl]-2-oleyl-3-(2-hydroxyethyl)imidazolinium chloride (DOTIM) and cholesterol, dimethyldioctadecylammonium bromide (DDAB) and cholesterol, and combinations thereof. A most preferred liposome composition for use as a delivery vehicle includes DOTIM and cholesterol.

A suitable nucleic acid molecule includes any nucleic acid sequence such as coding or non-coding sequence, and DNA or RNA. Coding nucleic acid sequences encode at least a portion of a protein or peptide, while non-coding sequence does not encode any portion of a protein or peptide. According to the present invention, "non-coding" nucleic acids can include regulatory regions of a transcription unit, such as a promoter region. The term, "empty vector" can be used interchangeably with the term "non-coding", and particularly refers to a nucleic acid sequence in the absence of a protein coding portion, such as a plasmid vector without a gene insert. Expression of a protein encoded by the nucleic acid molecule is not required for elicitation of a non-antigen-specific immune response; therefore the nucleic acid molecule does not necessarily need to be operatively linked to a transcription control sequence. However, further advantages may be obtained (i.e., antigen-specific and enhanced immunity) by including in the composition nucleic acid sequence (DNA or RNA) which encodes an immunogen and/or a cytokine.

Complexing a liposome with a nucleic acid molecule may be achieved using methods standard in the art or as described in U.S. Pat. No. 6,693,086, and incorporated herein by reference. A suitable concentration of a nucleic acid molecule to add to a liposome includes a concentration effective for delivering a sufficient amount of nucleic acid molecule into a subject such that a systemic immune response is elicited. In one embodiment, from about 0.1 µg to about 10 µg of nucleic acid molecule is combined with about 8 nmol liposomes, in another embodiment, from about 0.5 µg to about 5 µg of nucleic acid molecule is combined with about 8 nmol liposomes, and in yet another embodiment, about 1.0 µg of nucleic acid molecule is combined with about 8 nmol liposomes. In one embodiment, the ratio of nucleic acids to lipids (µg nucleic acid:nmol lipids) in a composition is at least about 1:1 nucleic acid:lipid by weight (i.e., 1 µg nucleic acid: 1 nmol lipid), and in another embodiment, at least about 1:5, and in yet another embodiment, at least about 1:10, and in a further embodiment at least about 1:20. Ratios expressed herein are based on the amount of cationic lipid in the composition, and not on the total amount of lipid in the composition. In another embodiment, the ratio of nucleic acids to lipids in a composition of the invention is from about 1:1 to about 1:80 nucleic acid:lipid by weight; and in another embodiment, from about 1:2 to about 1:40 nucleic acid:lipid by weight; and a further embodiment, from about 1:3 to about 1:30 nucleic acid:lipid by weight; and in yet another embodiment, from about 1:6 to about 1:15 nucleic acid:lipid by weight.

b. Biological Agent

In another embodiment of the invention, the immunomodulator includes a liposome delivery vehicle, a nucleic acid molecule, and at least one biological agent.

Suitable biological agents are agents that are effective in preventing or treating bovine disease. Such biological agents include immune enhancer proteins, immunogens, vaccines, antimicrobials or any combination thereof. Suitable immune enhancer proteins are those proteins known to enhance immunity. By way of a non-limiting example, a cytokine, which includes a family of proteins, is a known immunity enhancing protein family. Suitable immunogens are proteins which elicit a humoral and/or cellular immune response such that administration of the immunogen to a subject mounts an immunogen-specific immune response against the same or similar proteins that are encountered within the tissues of the subject. An immunogen may include a pathogenic antigen expressed by a bacterium, a virus, a parasite or a fungus.

Preferred antigens include antigens which cause an infectious disease in a subject. According to the present invention, an immunogen may be any portion of a protein, naturally occurring or synthetically derived, which elicits a humoral and/or cellular immune response. As such, the size of an antigen or immunogen may be as small as about 5-12 amino acids and as large as a full length protein, including sizes in between. The antigen may be a multimer protein or fusion protein. The antigen may be purified peptide antigens derived from native or recombinant cells. The nucleic acid sequences of immune enhancer proteins and immunogens are operatively linked to a transcription control sequence, such that the immunogen is expressed in a tissue of a subject, thereby eliciting an immunogen-specific immune response in the subject, in addition to the non-specific immune response.

In another embodiment of the invention, the biological agent is a vaccine. The vaccine may include a live, infectious, viral, bacterial, or parasite vaccine or a killed, inactivated, viral, bacterial, or parasite vaccine. In one embodiment, one or more vaccines, live or killed viral vaccines, may be used in combination with the immunomodulator composition of the present invention. Suitable vaccines include those known in the art for the cattle species. Exemplary vaccines, without limitation, include those used in the art for protection against infectious bovine rhinotracheitis (IBR) (Type 1 bovine herpes virus (BHV1)), parainfluenza virus type 3 (PI3), bovine respiratory syncytial virus (BRSV), bovine viral diarrhea virus (BVDV Type 1 and 2), *Histophilus somni, Mycoplasma bovis*, and other diseases known in the art. In an exemplary embodiment, a vaccine for the protection against *Mannheimia haemolytica* may be used in combination with the immunomodulator composition of the present invention.

In yet another embodiment of the invention, the biological agent is an antimicrobial. Suitable antimicrobials include: quinolones, preferably fluoroquinolones, β-lactams, and macrolide-streptogramin-lincosamide (MLS) antibiotics.

Suitable quinolones include benofloxacin, binfloxacin, cinoxacin, ciprofloxacin, clinafloxacin, danofloxacin, difloxacin, enoxacin, enrofloxacin, fleroxacin, gemifloxacin, ibafloxacin, levofloxacin, lomefloxacin, marbofloxacin, moxifloxacin, norfloxacin, ofloxacin, orbifloxacin, pazufloxacin, pradofloxacin, perfloxacin, temafloxacin, tosufloxacin, sarafloxacin, gemifloxacin, and sparfloxacin. Preferred fluoroquinolones include ciprofloxacin, enrofloxacin, moxifloxacin, danofloxacin, and pradofloxacin. Suitable naphthyridones include nalidixic acid.

Suitable β-lactams include penicillins, such as benzathine penicillin, benzylpenicillin (penicillin G), phenoxymethylpenicillin (penicillin V), procaine penicillin, methicillin, oxacillin, nafcillin, cloxacillin, dicloxacillin, flucloxacillin, temocillin, amoxicillin, ampicillin, co-amoxiclav (amoxicillin and clavulanic acid), azlocillin, carbenicillin, ticarcillin, mezlocillin, piperacillin; cephalosporins, such as cefalonium, cephalexin, cefazolin, cefapririn, cefquinome, ceftiofur, cephalothin, cefaclor, cefuroxime, cefamandole, defotetan, cefoxitin, ceftriaxone, cefotaxime, cefpodoxime, cefixime, ceftazidime, cefepime, cefpirome; carbapenems and penems such as imipenem, meropenem, ertapenem, faropenem, doripenem, monobactams such as aztreonam (Azactam), tigemonam, nocardicin A, tabtoxinine-B-lactam; and β-lactamase inhibitors such as clavulanic acid, tazobactam, and sulbactam. Preferred β-lactams include cephalosporins, in particular, cefazolin.

Suitable MLS antibiotics include any macrolide, lincomycin, clindamycin, pirlimycin. A preferred lincosamide is pirlimycin.

Other antimicrobials include 2-pyridones, tetracyclines, sulfonamides, aminoglycosids, trimethoprim, dimetridazoles, erythromycin, framycetin, furazolidone, various pleuromutilins such as tiamulin, valnemulin, various, streptomycin, clopidol, salinomycin, monensin, halofuginone, narasin, robenidine, etc.

2. Methods a. Methods of Immune Stimulation

In one embodiment of the invention, an immune response is elicited in a member of the bovine species by administering an effective amount of an immunomodulator composition to the member of the bovine species. The effective amount is sufficient to elicit an immune response in the member of the bovine species. The immunomodulator includes a liposome delivery vehicle and a nucleic acid molecule.

In one embodiment, the effective amount of the immunomodulator is from about 1 micrograms to about 1000 micrograms per animal. In another embodiment, the effective amount of the immunomodulator is from about 5 micrograms to about 500 micrograms per animal. In yet another embodiment, the effective amount of the immunomodulator is from about 10 micrograms to about 100 micrograms per animal. In a further embodiment, the effective amount of the immunomodulator is from about 10 micrograms to about 50 micrograms per animal.

In another embodiment of the invention, an immune response is elicited in a member of the bovine species by administering an effective amount of an immunomodulator, which includes a liposome delivery vehicle, an isolated nucleic acid molecule, and a biological agent. It is contemplated that the biological agent may be mixed with or co-administered with the immunomodulator or independently thereof. Independent administration may be prior to or after administration of the immunomodulator. It is also contemplated that more than one administration of the immunomodulator or biological agent may be used to extend enhanced immunity. Furthermore, more than one biological agent may be co-administered with the immunomodulator, administered prior to the immunomodulator, administered after administration of the immunomodulator, or concurrently.

b. Diseases

The methods of the invention elicit an immune response in a subject such that the subject is protected from a disease that is amenable to elicitation of an immune response. As used herein, the phrase "protected from a disease" refers to reducing the symptoms of the disease; reducing the occurrence of the disease, and reducing the clinical or pathologic severity of the disease or reducing shedding of a pathogen causing a disease. Protecting a subject can refer to the ability of a therapeutic composition of the present invention, when administered to a subject, to prevent a disease from occurring, cure, and/or alleviate or reduce disease symptoms, clinical signs, pathology, or causes. Examples of clinical signs of BRD include lung lesions, increased temperature, depression (e.g. anorexia, reduced responsiveness to external stimuli, droopy ears), nasal discharge, and respiratory character (e.g. respiratory rate, respiratory effort). As such, to protect a member of the bovine species from a disease includes both preventing disease occurrence (prophylactic treatment) and treating a member of the bovine species that has a disease (therapeutic treatment). In particular, protecting a subject from a disease is accomplished by eliciting an immune response in the member of the bovine species by inducing a beneficial or protective immune response which may, in some instances, additionally suppress, reduce, inhibit, or block an overactive or harmful immune response. The term "disease" refers to any deviation from the normal health of a member of the bovine species and includes a state when disease symptoms are present, as well as conditions in which a deviation (e.g., infection, gene mutation, genetic defect, etc.) has occurred, but symptoms are not yet manifested.

Methods of the invention may be used for the prevention of disease, stimulation of effector cell immunity against disease, elimination of disease, alleviation of disease, and prevention of a secondary disease resulting from the occurrence of a primary disease.

The present invention may also improve the acquired immune response of the animal when co-administered with a vaccine versus administration of the vaccine by itself. Generally a vaccine once administered does not immediately protect the animal as it takes time to stimulate acquired immunity. The term "improve" refers, in the present invention, to elicitation of an innate immune response in the animal until the vaccine starts to protect the animal and/or to prolong the period of protection, via acquired immunity, given by the vaccine.

Methods of the invention include administering the composition to protect against infection of a wide variety of pathogens. The composition administered may or may not include a specific antigen to elicit a specific response. It is contemplated that the methods of the invention will protect the recipient subject from disease resulting from infectious microbial agents including, without limitation, viruses, bacteria, fungi, and parasites. Exemplary viral infectious diseases, without limitation, include those resulting from infection with infectious bovine rhinotracheitis (IBR) (Type 1 bovine herpes virus (BHV1)), parainfluenza virus type 3 (PI3), bovine respiratory syncytial virus (BRSV), bovine viral diarrhea virus (BVDV Type 1 and 2), bovine adenovirus, bovine coronavirus (BCV), bovine calicivirus, bovine parvovirus, BHV4, bovine reovirus, bovine enterovirus, bovine rhinovirus, malignant catarrhal fever virus, bovine leukemia virus, rabies virus, Vesicular stomatitis virus (VSV), bluetongue (Orbivirus), recombinants thereof, and other viruses known in the art. Exemplary bacterial infections, without limitation, include those resulting from infection with gram positive or negative bacteria and Mycobacteria such as *Escherichia coli, Pasteurella multocida, Clostridium perfringens, Clostridium colinum, Campylobacter jejuni, Clostridium botulinum, Clostridium novyi, Clostridium chauveoi, Clostridium septicum, Clostridium hemolyticum, Clostridium tetani, Mannheimia haemolytica, Ureaplasma diversum, Mycoplasma dispar, Mycoplasma bovis, Mycoplasma bovirhinis, Histophilus somni, Campylobacter fetus, Leptospira* spp., *Arcanobacterium pyogenes, Bacillus anthrax, Fusobacterium necrophorum, Fusobacterium* spp., *Treponema* spp., *Corynebacterium, Brucella abortus, Mycobacterium paratuberculosis, Mycobacterium* spp., *Histophilus* spp., *Moraxella* spp., *Muellerius* spp., *Mycoplasma* spp., *Salmonella* spp., *Bacillus anthraci*s, and other bacteria known in the art. Exemplary fungi or mold infection, without limitation, include those resulting from infection with *Actinobacterim* spp., *Aspergillus* spp., and *Histomonas* spp., and other infectious fungi or mold known in the art. Exemplary parasites include, without limitation, *Neospora* spp., *Trichostrongylus, Cooperia, Anaplasma* spp, *Babesia* spp, *Chorioptes* spp, *Cysticercus* spp, *Dermatophilus* spp, *Damalinia bovis, Dictylocaulus* spp, *Eimeria* spp,

*Eperythrozoon* spp, *Haemonchus* spp, *Melophagus* spp, *Muellerius* spp, *Nematodirus* spp, *Oestrus* spp, *Ostertagia* spp, *Psoroptes* spp, *Sarcoptes* spp, *Serpens* spp, *Strongyloides* spp, *Toxoplasma* spp, *Trichuris* spp, *Trichophyton* spp, and *Tritrichomas* spp, *Fascioloides* spp, *Anaplasma marginale*, and other parasites known in the art.

c. Subjects

The methods of the invention may be administered to any subject or member of the bovine species, whether domestic or wild. In particular, it may be administered to those subjects that are commercially reared for breeding, meat or milk production. Suitable bovine subjects, without limitation, include antelopes, buffalos, yaks, cattle, and bison. In one embodiment, the member of the bovine species is cattle. Species of cattle include, without limitation, cows, bulls, steers, heifer, ox, beef cattle, or dairy cattle. A skilled artisan will appreciate that the methods of the invention will be largely beneficial to cattle reared for breeding, meat or milk production, since they are especially vulnerable to environmental exposure to infectious agents.

d. Administration

A variety of administration routes are available. The particular mode selected will depend, of course, upon the particular biological agents selected, the age and general health status of the subject, the particular condition being treated and the dosage required for therapeutic efficacy. The methods of this invention may be practiced using any mode of administration that produces effective levels of an immune response without causing clinically unacceptable adverse effects. The compositions may conveniently be presented in unit dosage form and may be prepared by any of the methods well known in the art.

Vaccination of the bovine species can be performed at any age. The vaccine may be administered intravenously, intramuscularly, intradermal, intraperitoneal, subcutaneously, by spray/aerosol, orally, intraocularly, intratracheally, intranasal, or by other methods known in the art. Further, it is contemplated that the methods of the invention may be used based on routine vaccination schedules. The immunomodulator may also be administered intravenously, intramuscularly, subcutaneously, by spray, orally, intraocularly, intratracheally, nasally, or by other methods known in the art. In one embodiment, the immunomodulator is administered subcutaneously. In another embodiment, the immunomodulator is administered intramuscularly. In yet another embodiment, the immunomodulator is administered as a spray. In a further embodiment, the immunomodulator is administered orally.

In one embodiment, the immunomodulator is administered by itself to the animal prior to challenge (or infection). In another embodiment, the immunomodulator is administered by itself to the animal post challenge (or infection). In yet another embodiment, the immunomodulator is administered by itself to the animal at the same time as challenge (or infection). In a further embodiment, the immunomodulator composition is co-administered at the same time as the vaccination prior to challenge. In yet a further embodiment, the immunomodulator composition is co-administered at the same time as the vaccination at the same time as challenge (or infection). The co-administration may include administering the vaccine and immunomodulator in the same general location on the animal at two different sites next to each other (i.e., injections next to each other at the neck of the animal), on opposing sides of the animal at the same general location (i.e., one on each side of the neck), or on different locations of the same animal. In another embodiment, the immunomodulator composition is administered prior to vaccination and challenge. In a further embodiment, the immunomodulator composition is administered after vaccination but prior to challenge. In a further embodiment, the immunomodulator composition is administered after challenge to an animal that has been vaccinated prior to challenge (or infection).

In one embodiment, the immunomodulator is administered from about 1 to about 14 days prior to challenge or from about 1 to about 14 days post challenge. In another embodiment, the immunomodulator is administered from about 1 to about 7 days prior to challenge or from about 1 to about 7 days post challenge. In yet another embodiment, the immunomodulator is administered 1, 2, 3, 4, 5, 6, 7 days prior to challenge or 1, 2, 3, 4, 5, 6, 7 days post challenge.

Other delivery systems may include time-release, delayed release or sustained release delivery systems. Such systems can avoid repeated administrations of the compositions therefore increasing convenience. Many types of release delivery systems are available and known to those of ordinary skill in the art. They include polymer based systems such as poly(lactide-glycolide), copolyoxalates, polycaprolactones, polyesteram ides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are lipids including sterols such as cholesterol, cholesterol esters and fatty acids or neutral fats such as mono-di and tri-glycerides; hydrogel release systems; sylastic systems; peptide based systems; wax coatings; compressed tablets using convention binders and excipients; partially fused implants; and the like. Specific examples include, but are not limited to erosional systems in which an agent of the invention is contained in a form within a matrix such as those described in U.S. Pat. Nos. 4,452,775, 4,675,189 and 5,736,152, and diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

As various changes could be made in the above composition, products and methods without departing from the scope of the invention, it is intended that all matter contained in the above description and in the examples given below, shall be interpreted as illustrative and not in a limiting sense.

Definitions

The term "effective amount" refers to the amount necessary or sufficient to realize a desired biologic effect. For example, an effective amount of immunomodulator for treating or preventing an infectious disease is that amount necessary to cause the development of an immune response upon exposure to the microbe, thus causing a reduction in the amount of microbe within the subject and preferably to the eradication of the microbe. The effective amount for any particular application can vary depending on such factors as the disease or condition being treated, the size of the subject, or the severity of the disease or condition. One of ordinary skill in the art can empirically determine the effective amount of immunomodulator without necessitating undue experimentation.

The term "cytokine" refers to an immune enhancing protein family. The cytokine family includes hematopoietic growth factor, interleukins, interferons, immunoglobulin superfamily molecules, tumor necrosis factor family molecules and chemokines (i.e. proteins that regulate the migration and activation of cells, particularly phagocytic cells). Exemplary cytokines include, without limitation, interleukin-2 (IL-2), interleukin-12 (IL12), interleukin-15 (IL-15), interleukin-18 (IL-18), interferon-α (IFNα), and interferon-γ (IFNγ).

The term "elicit" can be used interchangeably with the terms activate, stimulate, generate or upregulate.

The term "eliciting an immune response" in a subject refers to specifically controlling or influencing the activity of the immune response, and can include activating an immune response, upregulating an immune response, enhancing an immune response and/or altering an immune response (such as by eliciting a type of immune response which in turn changes the prevalent type of immune response in a subject from one which is harmful or ineffective to one which is beneficial or protective).

The term "operatively linked" refers to linking a nucleic acid molecule to a transcription control sequence in a manner such that the molecule is able to be expressed when transfected (i.e., transformed, transduced or transfected) into a host cell. Transcriptional control sequences are sequences which control the initiation, elongation, and termination of transcription. Particularly important transcription control sequences are those which control transcription initiation, such as promoter, enhancer, operator and repressor sequences. A variety of such transcription control sequences are known to those skilled in the art. Preferred transcription control sequences include those which function in avian, fish, mammalian, bacteria, plant, and insect cells. While any transcriptional control sequences may be used with the invention, the sequences may include naturally occurring transcription control sequences naturally associated with a sequence encoding an immunogen or immune stimulating protein.

The terms "nucleic acid molecule" and "nucleic acid sequence" can be used interchangeably and include DNA, RNA, or derivatives of either DNA or RNA. The terms also include oligonucleotides and larger sequences, including both nucleic acid molecules that encode a protein or a fragment thereof, and nucleic acid molecules that comprise regulatory regions, introns, or other non-coding DNA or RNA. Typically, an oligonucleotide has a nucleic acid sequence from about 1 to about 500 nucleotides, and more typically, is at least about 5 nucleotides in length. The nucleic acid molecule can be derived from any source, including mammalian, fish, bacterial, insect, viral, plant, or synthetic sources. A nucleic acid molecule can be produced by methods commonly known in the art such as recombinant DNA technology (e.g., polymerase chain reaction (PCR), amplification, cloning) or chemical synthesis. Nucleic acid molecules include natural nucleic acid molecules and homologues thereof, including, but not limited to, natural allelic variants and modified nucleic acid molecules in which nucleotides have been inserted, deleted, substituted, or inverted in such a manner that such modifications do not substantially interfere with the nucleic acid molecule's ability to encode an immunogen or immune stimulating protein useful in the methods of the present invention. A nucleic acid homologue may be produced using a number of methods known to those skilled in the art (see, for example, Sambrook et al., *Molecular Cloning: A Laboratory Manual*, Cold Spring Harbor Labs Press, 1989), which is incorporated herein by reference. Techniques to screen for immunogenicity, such as pathogen antigen immunogenicity or cytokine activity are known to those of skill in the art and include a variety of in vitro and in vivo assays.

EXAMPLES

The following examples illustrate various embodiments of the invention.

Example 1

Evaluation of Cattle Receiving a DNA Immunomodulator Before or After Developing Natural Bovine Respiratory Disease The purpose of this study was to determine the efficacy of the DNA immunomodulator administered to calves prior to and after developing natural cases of BRD.

Immunomodulator

The immunomodulator used in this study was a composition comprising a cationic lipid and non-coding DNA. The synthetic immunomodulator lipid components [1-[2-[9-(Z)-octadecenoyloxy]]-2-[8](Z)-heptadecenyl]-3-[hydroxyethyl]imidazolinium chloride (DOTIM) and a synthetic neutral lipid cholesterol were formulated to produce liposomes approximately 200 nm in diameter (See, U.S. Pat. No. 6,693,086). The DNA component was a 4242 base-pair non-coding DNA plasmid produced in *E. coli*, which, being negatively charged, associates with the positively-charged (cationic) liposomes (See, U.S. Pat. No. 6,693,086).

Study Animals

84 Holstein steer calves of weaning age were selected from a herd without a current history of respiratory disease. Each individual calf was initially evaluated and determined to be in good health. The 84 calves were divided into seven treatment groups of 12 calves each. Only animals not vaccinated for *Mannheimia haemolytica* were included in the study. None of the animals had received an antimicrobial agent within 30 days prior to administration of DNA immunomodulator.

The treatment groups were administered varying doses of the DNA immunomodulator describe above on the day of treatment as indicated in Table 1.1 below. The dilution scheme of the DNA immunomodulator is provided in Table 1.2. The DNA immunomodulator was administered intramuscularly and cranial to the left shoulder, ventral to the nuchal ligament, and caudo-dorsal to the jugular groove of the calves.

As referred to below, Treatment Day −1 refers to the start date of the study after initial selection in which the calves were evaluated and determined to be suitable for the study. Treatment Day 0 is one day subsequent to Day −1, and so on.

TABLE 1.1

Administration Schedule of Immunomodulator

| Treatment number | DNA Immunomodulator Dose (μg) | Day of Immunomodulator Administration | Animals per Treatment group |
|---|---|---|---|
| 1 | 500 | −1 | 12 |
| 2 | 200 | −1 | 12 |
| 3 | 50 | −1 | 12 |
| 4 | 500 | 0 | 12 |
| 5 | 200 | 0 | 12 |
| 6 | 50 | 0 | 12 |
| 7 | 0 (Control) | NA | 12 |

A large proportion of the calves were observed to be experiencing variable levels of BRD on the morning of Day 0. By Day 5 all of the calves remaining in the study population were observed to have met the case definition for BRD morbidity. Cattle were only removed from the study population if euthanasia was indicated due to severe BRD. No other infectious/non-infectious diseases were observed and thereby required removal in this study.

Evaluation

On Days 1-5 of the study the calves were evaluated for various health indicators. For example, rectal temperature and average daily weight were determined for each of the calves per day through the length of the study. Animals were evaluated at approximately the same time each day (+/−3 hours) from Day 1 to Day 5. FIGS. 1.1 and 1.2 present the averages of rectal temperatures and average daily weight gain according to dose of immunomodulator administered.

On Day 5, all calves were euthanized and necropsied. Lung lesion scores were determined (based upon the degree lung consolidation estimated by visual inspection and manual palpation) for each individual calf at the time of necropsy.

FIG. 1.3 presents the lung lesion scores with respect to dose of immunomodulator administered. The overall lung lesion scores for each day of administration were approximately 11% and 14% for Day −1 and Day 0, respectively. Lung lesion scores of 11.2%, 9.0%, 10.8% and 19.9% were exhibited for 500, 200, 50 and negative control groups, respectively. The largest difference between the control group and a treated group (200 µg) was about an 11% A reduction.

Model-adjusted estimates on FIG. 1.3 reflect the raw averages that are adjusted for all statistical model covariates (i.e. dose, day, and dose x day) as well as for the pen in which the calves were housed throughout the study. Therefore, model-adjusted estimates may display differences compared to the raw averages.

Subsequent bacteriology (lung cultures) and virology (nasal swabs) were also performed. Of the remaining calves (69) that were euthanized on Day 5, 11.6% were found to be shedding bovine herpes virus type 1 (BHV-1) in nasal secretions. With regard to lung cultures from all of the study animals, 41% were positive for Mh, 31.3% were culture positive for *Pasteurella multocida* (Pm), 10.8% were culture positive for both Mh and Pm, and no *Histophilus somni* was isolated throughout the study population. Cultures for *Mycoplasma bovis* were not performed in this study Results In this study, the dose of the DNA immunomodulator (i.e. 500 µg, 200 µg, and 50 µg) approached a significant reduction in lung lesion scores compared to the negative control (P=0.1284; See FIG. 1.3). However, the day of DNA immunomodulator administration (i.e., Day −1 or 0) was not significantly associated with lung lesion scores. No statistical differences in lung lesion scores were observed among the DNA immunomodulator dose groups. Rectal temperature tended to be significantly associated with the dose of DNA immunomodulator (P=0.1190) but was not associated with the day of administration. No obvious differences were observed between the dose of the DNA immunomodulator and the negative control with regard to average daily weight gain.

There was a strong tendency for the DNA immunomodulator to reduce lung lesions compared to negative control, thereby, providing evidence that this product has the potential to protect lung tissue during a BRD outbreak. In this study, the day of treatment administration was not associated with lung lesions thereby indicating that it does not matter if cattle received the DNA immunomodulator one day prior or the same day as the onset of clinical signs associated with BRD. This outcome is important as the timing of exposure to BRD pathogens is generally unknown among typical production systems and is further complicated by the impact of various stressors experienced by cattle throughout the chain of production. Therefore, providing producers with a product that offers flexibility in the timing of administration, in relation to the onset of BRD, is of extreme value in the beef and dairy industries.

Example 2

Evaluation of Cattle Receiving a DNA Immunomodulator Concurrently with or One Day After an Experimental Challenge with *Mannheimia Haemolytica*

The purpose of this study was to determine the efficacy of the DNA immunomodulator administered to calves concurrently with or one day after an experimental challenge with *Mannheimia haemolytica*.

Immunomodulator

The immunomodulator used in this study was the composition described above in Example 1.

Study Animals

84 Holstein steer calves of weaning age and weighing on average about 300 lbs (136 kg) were selected from a herd without a current history of respiratory disease. Each individual calf was initially evaluated and determined to be in good health. The 84 calves were divided into seven treatment groups of 12 calves each. Only animals not vaccinated for *Mannheimia haemolytica* were included in the study. None of the animals had received an antimicrobial agent within 30 days prior to administration of DNA immunomodulator. The treatment groups were administered varying doses of the DNA immunomodulator on the day of treatment as indicated in Table 2.1 below. The dilution scheme of the DNA immunomodulator is provided in Table 2.2. The DNA immunomodulator was administered intramuscularly and cranial to the left shoulder, ventral to the nuchal ligament, and caudo-dorsal to the jugular groove of the calves.

As referred to below, Treatment Day 0 refers to the start date of the study after initial selection in which the calves were evaluated and determined to be in good health. Treatment Day 1 is one day subsequent to Day 0, and so on.

TABLE 2.1

Administration Schedule of Immunomodulator and Mh Challenge

| Treatment number | DNA Immunomodulator Dose (µg) | Day of Immunomodulator Administration | Day of Mh Challenge Administration | Animals per Treatment group |
|---|---|---|---|---|
| 1 | 500 | 0 | 0 | 12 |
| 2 | 200 | 0 | 0 | 12 |
| 3 | 50 | 0 | 0 | 12 |
| 4 | 500 | 1 | 0 | 12 |

TABLE 2.1-continued

Administration Schedule of Immunomodulator and Mh Challenge

| Treatment number | DNA Immunomodulator Dose (μg) | Day of Immunomodulator Administration | Day of Mh Challenge Administration | Animals per Treatment group |
|---|---|---|---|---|
| 5 | 200 | 1 | 0 | 12 |
| 6 | 50 | 1 | 0 | 12 |
| 7 | 0 (Control) | NA | 0 | 12 |

Experimental Challenge

On Day 0, the calves were challenged a total of $3.12 \times 10^7$ colony forming units (CFU) of *Mannheimia haemolytica*. The inoculum was administered via the respiratory tract. By Day 3, all of the calves in the study population were observed to have met the case definition for BRD morbidity. The median day of onset was one day.

Evaluation

As in the previous example, on Days 1-5 of the study the calves were evaluated for various health indicators. Rectal temperature and average daily weight were determined for each of the calves per day through the length of the study. Animals were evaluated at approximately the same time each day. FIGS. 2.1 and 2.2 present the averages of rectal temperatures and average daily weight gains with respect to dose of immunomodulator administered.

On Day 5, all calves were euthanized and necropsied. Lung lesion scores were determined for each individual calf at the time of necropsy according to the formula described in Example 1.

FIG. 2.3 presents the model-adjusted lung lesion scores with respect to dose of immunomodulator administered.

Results

In this study, the dose of the DNA immunomodulator (i.e. 500 μg, 200 μg, and 50 μg) significantly reduced lung lesion scores compared to the negative control. However, the lower doses (200 μg, and 50 μg) outperformed the 500 μg dose in reducing lung lesions. The day of DNA immunomodulator administration (i.e., Day 0 or 1) was not significantly associated with lung lesion scores. No statistical differences in lung lesion scores were observed among the DNA immunomodulator dose groups. Rectal temperature was significantly reduced in calves administered the DNA immunomodulator compared to the negative control, but was not associated with dose. No obvious differences were observed between the dose of the DNA immunomodulator and the negative control with regard to average daily weight gain.

There was a strong tendency for the DNA immunomodulator to reduce lung lesions compared to negative control, thereby, providing evidence that this product has the potential to protect lung tissue during a BRD outbreak. In this study, the day of treatment administration was not associated with lung lesions thereby indicating that it did not matter if cattle received the DNA immunomodulator one day prior, or the same day as, the onset of clinical signs associated with BRD. This outcome is important as the timing of exposure to BRD pathogens is generally unknown among typical production systems and is further complicated by the impact of various stressors experienced by cattle throughout the chain of production. Therefore, providing producers with a product that offers flexibility in the timing of administration, in relation to the onset of BRD, is of extreme value in the beef and dairy industries.

Example 3

Evaluation of Cattle Receiving a DNA Immunomodulator Two Days Before or Concurrently with an Experimental Challenge with *Mannheimia Haemolytica*

The purpose of this study was to determine the efficacy of the DNA immunomodulator administered to calves two days before or concurrently with an experimental challenge with *Mannheimia haemolytica*.

Immunomodulator

The immunomodulator used in this study was the composition described above in Example 1.

Study Animals

96 Holstein steer calves weighing on average about 800-1000 lbs (363-454 kg) were selected from a herd without a current history of respiratory disease. Each individual calf was initially evaluated and determined to be in good health. The 96 calves were divided into eight treatment groups of 12 calves each. Only animals not vaccinated for *Mannheimia haemolytica* were included in the study. None of the animals had received an antimicrobial agent within 30 days prior to administration of DNA immunomodulator. The treatment groups were administered varying doses of the DNA immunomodulator on the day of treatment as indicated in Table 3.1 below. The dilution scheme of the DNA immunomodulator is provided in Table 3.2. The DNA immunomodulator was administered intramuscularly and cranial to the left shoulder, ventral to the nuchal ligament, and caudo-dorsal to the jugular groove of the calves. As referred to below, Treatment Day −2 refers to the start date of the study when Treatment Groups 1-3 were administered the immunomodulator. Treatment Day 0 is two days subsequent to Day −2, and so on.

TABLE 3.1

Administration Schedule of Immunomodulator and Mh Challenge

| Treatment number | DNA Immunomodulator Dose (μg) | Day of Immunomodulator Administration | Day of Mh Challenge Administration | Animals per Treatment group |
|---|---|---|---|---|
| 1 | 200 | −2 | 0 | 12 |
| 2 | 50 | −2 | 0 | 12 |
| 3 | 25 | −2 | 0 | 12 |
| 4 | 200 | 0 | 0 | 12 |
| 5 | 50 | 0 | 0 | 12 |

TABLE 3.1-continued

Administration Schedule of Immunomodulator and Mh Challenge

| Treatment number | DNA Immunomodulator Dose (μg) | Day of Immunomodulator Administration | Day of Mh Challenge Administration | Animals per Treatment group |
|---|---|---|---|---|
| 6 | 25 | 0 | 0 | 12 |
| 7 | 0 (Control) | −2 | 0 | 12 |
| 8 | 0 (Control) | 0 | 0 | 12 |

Experimental Challenge

On Day 0, the calves were challenged with a total of $1.9 \times 10^{10}$ CFUs. The inoculum was administered via the respiratory tract.

Evaluation

As in the previous examples, on Days 1-5 of the study the calves were evaluated for various health indicators. On Day 5, all calves were euthanized and necropsied. Lung lesion scores were determined for each individual calf at the time of necropsy.

FIG. 3.1 presents the model-adjusted lung lesion scores with respect to dose of immunomodulator administered. FIG. 3.2 presents the model-adjusted lung lesion scores with respect to day of immunomodulator administration.

Results

In this study, the dose of the DNA immunomodulator (i.e. 200 μg, 50 μg, and 25 μg) significantly reduced lung lesion scores compared to the negative controls. However, no statistical differences in lung lesion scores were observed among the DNA immunomodulator dose groups. The day of DNA immunomodulator administration (i.e. Days −2 and 0) was significantly associated with lung lesion scores. Significant reduction in lung lesions was observed when the immunomodulator was administered on Day 0 when compared to Day −2.

Example 4

Mh Challenge Co-Administration of Immunomodulator and Killed Mh Vaccine

The purpose of this study was to determine the efficacy of the DNA immunomodulator co-administered with killed Mh vaccine to calves subjected to an experimental challenge with *Mannheimia haemolytica*.

Immunomodulator

The immunomodulator used in this study was the composition described above in Example 1.

Study Animals

81 Holstein bull calves, 12 weeks old, were selected from a herd without a current history of respiratory disease. Each individual calf was evaluated and determined to be in good health. Only animals not vaccinated for *Mannheimia haemolytica* were included in the study. None of the animals had received an antimicrobial agent within 30 days prior to administration of inoculum.

Experimental Infection and Challenge

The challenge, or experimental infection, included exposure to an inoculum of *Mannheimia haemolytica*. The organisms were used at a concentration of $1.7 \times 10^8$ per animal for the first inoculum and $2.4 \times 10^{10}$ animal for the second inoculum. The animals were also challenged with a spray by another respiratory route. The concentration of the organisms in the spray inoculum was $1.9 \times 10^{10}$ per animal.

The efficacy of the immunomodulator, as described above, administered to calves followed by exposure to *Mannheimia haemolytica* was determined by the twelve treatment groups as detailed on Table 3.

TABLE 4.3

Study Treatment Groups.

| Group | Targeted Dose | Treatment Day | Days Contact | Number of Animals |
|---|---|---|---|---|
| T1 | Killed MH (oil) vaccine (SC) | 0 | X | 7 |
| T2 | Killed MH (oil) vaccine + Immunomodulator 500 μg (SC) | 0 | X | 7 |
| T3 | Killed MH (oil) vaccine (SC) | 7 | X | 6 |
| T4 | Killed MH (oil) vaccine + Immunomodulator 500 μg (SC) | 7 | X | 7 |
| T5 | Immunomodulator 500 μg (SC) | 7 | X | 7 |
| T6 | Immunomodulator 500 μg (SC) | 13 | X | 7 |
| T7 | Immunomodulator 500 μg (IM) | 13 | X | 7 |
| T8 | Immunomodulator 500 μg (SC) | 15* | X | 7 |
| T9 | Control NC | NA | NA | 7 |
| T10 | Control CC | NA | X | 5 |
| T11 | Control SE | NA | X | 7 |
| T12 | Killed MH (aqueous) vaccine + Immunomodulator 500 μg (SC) | 0 | X | 7 |

Oil MH = *Mannheimia haemolytica* vaccine (Pulmo-Guard ® PHM)
Aqueous MH = *Mannheimia haemolytica* vaccine (One Shot ®)
NC = Not commingled and not spray challenged (for background gross pathology)
CC = Contact and spray challenged
SE = Used as Seeder challenge (Challenged intratracheal)
All animals, except SE and NC were spray challenged
SC = Subcutaneous route of injection
IM = Intramuscular route of injection
NA = Not Applicable
*Animals in group T8 will be treated after intranasal challenge On day 0 of the study, all animals in groups T1, T2 and T12 were administered the immunomodulator subcutaneously. The immunomodulator was administered subcutaneously on Day 7 to Groups T3, T4, and T5. The immunomodulator was administered subcutaneously on Day 13 to Group T6 and intramuscularly to T7. The immunomodulator was administered subcutaneously on Day 15 to Group T8.

All animals receiving the vaccine were vaccinated according to label instructions. Immunomodulator and the vaccine were administered as close together near a lymph node (neck)—two injections (one for vaccine and the other for the immunomodulator). All animals receiving the subcutaneous route of injection were injected near a lymph node in the sub scapular region.

On study day 10, all T11 calves were transported off site in a stock trailer for approximately 24 hours to stress the calves. On Study day 11, 20 mL of an inoculum containing *Mannheimia haemolytica* was administered transtracheally to all the T11 animals, followed 4 hours later with 25 mL of inoculum. On study day 14, all groups, except T9 were commingled and transported off site in a stock trailer for approximately 24 hours to stress the calves. All animals except in group NC were commingled in a large pen for 12 to 16 hours on Study day 14 and then returned to their separate pens (each animal had a separate pen). On Study day 15, 20 mL of *Mannheimia haemolytica* was administered by another respiratory route to all groups except T9 and T11. The animals were observed daily throughout the study for clinical abnormalities and mortality. All animals were negative or had low titers at screening prior to purchase of animals. The animals had high titers prior to treatment, which indicates that the animals serologically converted to *Mannheimia haemolytica* prior to receiving treatment.
Results The animals of group T8 had significantly lower lung lesions.

The study suggests that there is an onset of early protection (day 7) with or without vaccine (groups T4 and T5 compared to T3). See FIGS. 4.1 and 4.2.

Example 5

Evaluation of Acquired Immunity in Cattle Vaccinated with a Commercial-Live Vaccine when Co-Administered with a DNA Immunomodulator The purpose of this study was to determine if co-administration of the DNA immunomodulator augmented the acquired immunity afforded by modified-live viral (MLV) vaccines.
Immunomodulator The immunomodulator used in this study was the composition described above in Example 1.
Study Animals 72 Holstein steers calves of weaning age were selected from a herd without a current history of respiratory disease. The 72 calves were divided into six treatment groups of 12 calves each. Each individual calf was evaluated and determined to be in good health. All calves were free of serum antibodies to BHV-1, BVDV types 1 and 2, and BRSV. In addition, all calves were found to be serum antibody negative to PI-3. The calves were subsequently determined to be negative for bovine viral diarrhea virus persistent infection by immunohistochemistry.

The treatment groups were administered the vaccine and varying doses of the DNA immunomodulator intramuscularly on the day of treatment as indicated in Table 5.1 below. The dilution scheme of the DNA immunomodulator is provided in Table 5.2. On day 0 of the study, all animals in groups T1-T4 were administered the immunomodulator. All animals receiving the vaccine were vaccinated according to label instructions. Immunomodulator and the vaccine were administered as close together cranial to the front of the shoulder—two injections (one for vaccine and the other for the immunomodulator).

TABLE 5.1

Administration Schedule of Immunomodulator and Vaccine

| Group | Targeted Dose | Day of Vaccine and/or Immunomodulator Administration | Number of Animals |
|---|---|---|---|
| T1 | MLV + Immunomodulator (500 μg) IM | 0 | 12 |

TABLE 5.1-continued

Administration Schedule of Immunomodulator and Vaccine

| Group | Targeted Dose | Day of Vaccine and/or Immunomodulator Administration | Number of Animals |
|---|---|---|---|
| T2 | MLV + Immunomodulator (200 μg) IM | 0 | 12 |
| T3 | MLV + Immunomodulator (100 μg) IM | 0 | 12 |
| T4 | MLV + Immunomodulator (50 μg) IM | 0 | 12 |
| T5 | MLV | 0 | 12 |
| T6 | No treatment | NA | 12 |

MLV = *Mannheimia haemolytica* vaccine (Bovi-shield ®) - modified-live 4-way viral respiratory vaccine
IM = Intramuscular route of injection Evaluation Immunological testing was performed on samples from appropriate hematological specimens collected from the calves on Days 0, 13, 28, 27, 34 and 41. Cell mediated immunity (CMI) measurements were conducted for each specimen. The target pathogens for this study were BHV-1, BVDV 1 and 2, and BRSV. Laboratories used standardized procedures and methods as appropriate for the previously specified target pathogens.
Results Model-adjusted data for CMI outcomes on each Day of sample collection among all treatment groups were determined. Across all treatment groups, cell types, and antigens no statistical differences (P>0.10) were detected when comparing DNA immunomodulator treatment groups—MLV vaccine combinations to cattle receiving only the MLV vaccine (See FIGS. 5.1-5.12). In particular, FIGS. 5.1-5.4 present the measurements of the CD 25 E1 expression index (y-axis) across all five cell types for each of the 6 treatment groups (x-axis). FIGS. 5.5-5.8 present the measurements of the IFNγ expression index (y-axis) across all five cell types for each of the 6 treatment groups (x-axis). FIGS. 5.9-5.12 present the measurements of the IL-4 expression index (y-axis) across all five cell types for each of the 6 treatment groups (x-axis). Estimates were produced for each of the 4 BRD viral pathogens represented in their respective graph. For these statistical evaluations, all comparisons were made to the "MLV only" treatment group.

Statistically significant (P<0.10) treatment×Day interactions were detected for BVDV 1 (Days 28 and 35) and BVDV 2 (Day 42). No significant findings (P>0.10) were detected for BHV-1 at any of the listed time points. A graphical representation of these findings is displayed on FIGS. 5.13-5.15. The BRSV data was removed from analysis due to observance of antibody seroconversion within the negative control treatment group. Note that, for all statistical evaluations, all comparisons were made to the "MLV only" treatment group.

Individual animal weights were also collected during the study. A graphical representation of model-adjusted average daily gain outcomes is displayed in FIG. 5.16. No significant findings (P>0.10) were detected across treatment groups when compared to the MLV only group.

In summary, the DNA immunomodulator did not enhance CMI when co-administered with a MLV vaccine compared to the sole administration of MLV vaccine. However, 500 μg of the DNA immunomodulator may augment humoral immunity when co-administered with a MLV vaccine (specifically BVDV). Nonetheless, it should be noted that despite a lack of consistent improvement in acquired immunity, co-administration of the DNA immunomodulator, at doses of 500 µg, 200 µg, 100 µg, and 50 µg, did not impair the positive immunologic effects induced by the MLV vaccine. In addition, performance (e.g. ADG) was not negatively impacted by administration of the DNA immunomodulator.

Example 6

Evaluation of Acquired Immunity in Cattle Vaccinated with a Commercial-Vaccine when Co-Administered with a DNA Immunomodulator The purpose of this study was to determine if co-administration of the DNA immunomodulator augmented the acquired immunity afforded by vaccines containing inactivated antigens.

Immunomodulator

The immunomodulator used in this study was the composition described above in Example 1.

Study Animals

48 Holstein female cattle of 3-5 month age were selected from a herd without a current history of respiratory disease. The 48 cattle were divided into six treatment groups of 8 animals each. Each individual animal was evaluated and determined to be in good health. All animals were free of serum antibodies to BHV-1, BVDV types 1 and 2. The animals were also determined to be negative for bovine viral diarrhea virus persistent infection by PCR. The animals were not selected on SNT titers against BRS virus and PI3 virus.

The treatment groups were administered the vaccine and varying doses of the DNA immunomodulator intramuscularly on the day of treatment as indicated in Table 5.1 below. The vaccine contained BHV1 and BVDV type 1 and 2 as inactivated antigens, and modified live PI3 virus and BRS virus. The Immunomodulator and the vaccine were either given separately on the same side of the animal cranial to the front of the shoulder, or separately on the opposite side of the animal in the same region, or mixed in one syringe. The dilution scheme of the DNA immunomodulator is provided in Table 5.2.

TABLE 6.1

Administration Schedule of Immunomodulator and Vaccine

| Group | Targeted Dose | Day of Vaccine and/or Immunomodulator Administration | Number of Animals |
|---|---|---|---|
| T1 | Placebo (Dextrose 5%) | 0 | 8 |
| T2 | Vaccine + Dextrose IM, separately | 0 | 8 |
| T3 | Vaccine + Immunomodulator (20 µg) IM, mixed | 0 | 8 |
| T4 | Vaccine + Immunomodulator (200 µg) IM, mixed | 0 | 8 |
| T5 | Vaccine + Immunomodulator (200 µg) IM, separately same side | 0 | 8 |
| T6 | Vaccine + Immunomodulator (200 µg) IM, separately opposite side | 0 | 8 |

Vaccine = combined (inactivated and modified live) 4-way viral respiratory vaccine (Rispoval ®)
IM = Intramuscular route of injection Evaluation Immunological testing was performed on samples from appropriate hematological specimens collected from the cattle on Days 0, 3, 5, 7, 9, 11, 14, 17, 20, 23 and 27. The target pathogens for this study were BHV-1, BVDV 1 and 2. For information also the antibody titers against BRS virus and PI3 virus were determined. Laboratories used standardized Serum Neutralization Tests (SNT) as procedures for the previously specified target pathogens.

Results

Statistically significant (P<0.010) treatment x Day interactions were detected for BHV1 (Day 27). No significant findings (P>0.10) were detected for all other time points for BHV1 and for BVDV type 1 at 2 at any of the listed time points. The results of the BRSV and PI3 titers were not further evaluated because the animals were not serologically negative at the beginning of the study. An effect of treatment could therefore not be verified. A graphical representation of these findings is displayed on FIGS. 6.1. Note that, for all statistical evaluations, all comparisons were made to the "Vaccine and Dextrose 5%" treatment group.

The invention claimed is:

1. A method for reducing clinical signs caused by *Mannheimia haemolytica* in cattle comprising administering to the cattle an immunomodulator composition consisting of:
   a. a cationic liposome delivery vehicle; and
   b. an isolated bacterially-derived nucleic acid molecule that does not code for an immunogen, which is produced in *Escherichia coli*,
   wherein the immunomodulator composition elicits a non-antigen specific systemic immune response,
   wherein the administering is performed intramuscularly, intradermally, subcutaneously, by spray/aerosol, orally, intraocularly, or intratracheally,
   and wherein the administration of the immunomodulator composition reduces clinical signs caused by *Mannheimia haemolytica* in cattle.

2. The method of claim 1, wherein the liposome delivery vehicle comprises multilamellar vesicle lipids or extruded lipids.

3. The method of claim 1, wherein the liposome delivery vehicle comprises N-[1-(2,3-dioleyloxy)propyl]-N,N,N-trimethylammonium chloride (DOTMA) and cholesterol; N[1-(2,3-dioleoyloxy)propyl]-N,N,N-trimethylammonium chloride (DOTAP) and cholesterol; 1-[2-(oleoyloxy)ethyl]-2-oleyl-3-(2-hydroxyethyl)imidazolinium chloride (DOTIM) and cholesterol; or dimethyldioctadecylammonium bromide (DDAB) and cholesterol.

4. The method of claim 1, wherein the immunomodulator composition comprises from 0.1 µg to 10 µg of the nucleic acid molecule.

5. The method of claim 1, wherein the clinical signs that are reduced comprise lung lesions and/or increased temperature.

6. The method of claim 1, wherein the nucleic acid molecule is a DNA plasmid.

7. The method of claim 1, wherein the administering is performed intramuscularly.

8. The method of claim 1, wherein the administering is performed subcutaneously.

9. The method of claim 1, wherein the liposome delivery vehicle comprises 1-[2-(oleoyloxy)ethyl]-2-oleyl-3-(2-hydroxyethyl)imidazolinium chloride (DOTIM) and cholesterol.

10. The method of claim 1, wherein the immunomodulator composition comprises from 5 µg to 500 µg of the nucleic acid molecule.

\* \* \* \* \*